(12) United States Patent
Kwon et al.

(10) Patent No.: US 10,125,183 B2
(45) Date of Patent: Nov. 13, 2018

(54) DECOY PEPTIDES INHIBITING BINDING OF AMIGO2 AND 3-PHOSPHOINOSITIDE-DEPENDENT KINASE 1

(71) Applicant: Curacle Co., Ltd., Seongnam-si (KR)

(72) Inventors: Young Guen Kwon, Seoul (KR); Hyo Jin Park, Seoul (KR)

(73) Assignee: Curacle Co., Ltd., Seongnam-si (KR)

( * ) Notice: Subject to any disclaimer, the term of this patent is extended or adjusted under 35 U.S.C. 154(b) by 28 days.

(21) Appl. No.: 15/195,844

(22) Filed: Jun. 28, 2016

(65) Prior Publication Data

US 2016/0376339 A1 Dec. 29, 2016

(30) Foreign Application Priority Data

Jun. 29, 2015 (KR) .................. 10-2015-0092548

(51) Int. Cl.
| C07K 14/70 | (2006.01) |
| C07K 14/705 | (2006.01) |
| G01N 33/50 | (2006.01) |
| A61K 38/00 | (2006.01) |

(52) U.S. Cl.
CPC .............. *C07K 14/70503* (2013.01); *C12Y 207/11001* (2013.01); *G01N 33/5011* (2013.01); *A61K 38/00* (2013.01); *G01N 2333/70503* (2013.01); *G01N 2333/912* (2013.01); *G01N 2800/7014* (2013.01)

(58) Field of Classification Search
CPC .............................................. C07K 14/70503
See application file for complete search history.

(56) References Cited

U.S. PATENT DOCUMENTS

| 2006/0241284 A1 | 10/2006 | Kuja-Panula et al. | |
| 2011/0097261 A1* | 4/2011 | Janatpour .......... | C07K 16/2803 424/1.49 |
| 2013/0023461 A1* | 1/2013 | Prestegarden ........... | C07K 7/08 514/3.3 |
| 2014/0127162 A1* | 5/2014 | Balazs ............... | A61K 48/0066 424/93.2 |
| 2014/0134237 A1* | 5/2014 | Johnson ................. | A61K 38/16 424/450 |

FOREIGN PATENT DOCUMENTS

| JP | 2002-506078 A | 2/2002 | |
| JP | 2006-525784 A | 11/2006 | |
| KR | 20090121724 A | 11/2009 | |
| KR | 20140050207 A | 4/2014 | |
| WO | WO 00/77026 | * 12/2000 | ............... C07K 2/06 |

OTHER PUBLICATIONS

Notice of Allowance dated Aug. 28, 2017 for Korean Application No. 20150092548, Kwon et al., "Amigo2 3-1 Decoy Peptides Inhibiting Binding of AMIGO2 and 3-phosphoinositide-dependent kinase 1," filed Jun. 29, 2015 (5 pages).

* cited by examiner

*Primary Examiner* — Amber D Steele
(74) *Attorney, Agent, or Firm* — Clark & Elbing LLP; Susan M. Michaud

(57) ABSTRACT

The present invention provides a decoy peptide or polypeptide capable of inhibiting the binding of AMIGO2 and 3-phosphoinositide-dependent kinase 1 (PDK1), and a pharmaceutical composition, containing the decoy peptide or polypeptide as an active ingredient, for preventing or treating cancer or an angiogenic disease. Furthermore, the present invention provides a method for screening a material for preventing or treating cancer or an angiogenic disease. According to the present invention, it is worth noting that the decoy peptide or polypeptide of the present invention induces apoptosis through the inhibition of the binding of AMIGO2 and 3-phosphoinositide-dependent kinase 1 (PDK1); reduces migration and adhesion of endothelial cells; significantly reduces vascular induction, survival, and growth. The decoy peptide or polypeptide of the present invention can contribute to the prevention or treatment of cancer or an angiogenic disease through the inhibition of Akt signaling, resulting from the inhibition of a direct interaction of the cytosolic domain of AMIGO2 and the PH domain of PDK1.

14 Claims, 33 Drawing Sheets
(20 of 33 Drawing Sheet(s) Filed in Color)
Specification includes a Sequence Listing.

FIG. 5E

```
AMIGO2  TPCPCKCKTK----------RQKNMLIQSNAHSSILSPGPASDASAD--ERKAGAGKRVVFLEPL  472
AMIGO1  TPCRCWCRGV----------EKPSSHQGDSLSSSMLSTTPNHDPMAGGDKDDGFDRRVAFLEPA  447
AMIGO3  PPCRCCRRACRCRRWPQTPSPLQELSAQSSVLSTTPPDAPSRK----------ASVHKRVVFLEPG  460
         .** *            **.**. *                  .:* ****

AMIGO2  KDTAAGQNGKVRLFPSEAVIAEGILKSTRGKSDSDSVNSVFSDTPFVAST  522
AMIGO1  G-PGQGQNGKLXPG-NTLPVPEATGKGQRRMSDPESVSSVFSDTPIVV-- 493
AMIGO3  R------RGLNGRVQLAVAEEFDLYNPG-GLQLKAGSESASSIGSEGPMTT-- 504
         *  **..              .    ....*,*; *. *...
```

FIG. 5F

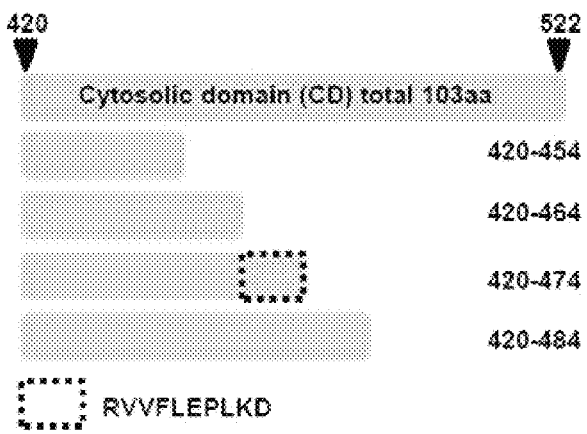

```
RVVFLEPLKD
```

DECOY PEPTIDES INHIBITING BINDING OF AMIGO2 AND 3-PHOSPHOINOSITIDE-DEPENDENT KINASE 1

TECHNICAL FIELD

The present invention was made with the support of the Ministry of Science, ICT and Future Planning, Republic of Korea, under Project No. NRF-2011-0019267, which was conducted in the program titled "Bio•Medical Technology Development Business" in the project named "Genomic studies on EC differentiation from UCB-EPCs and BM-derives MSCs", by the Industry-Academic Cooperation Foundation, YONSEI University, under management of the National Research Foundation of Korea, from 1 Jun. 2015 to 30 Apr. 2017.

Further, the present invention was made with the support of the Ministry of Science, ICT and Future Planning, Republic of Korea, under Project No. NRF-2013M3A9B6046563, which was conducted in the program titled "Bio•Medical Technology Development Business" in the project named "Cancer treatment technology development by identifying cancer blood vessels generation and non-normalized molecular regulatory mechanisms", by the Industry-Academic Cooperation Foundation, KANGWON University, under management of the National Research Foundation of Korea, from 1 Aug. 2014 to 31 Jul. 2015.

The present patent application claims priority to and the benefit of Korean Patent Application No. 10-2015-0092548 filed in the Korean Intellectual Property Office on Jun. 29, 2015, the disclosures of which are incorporated herein by reference.

The present invention relates to decoy peptides inhibiting binding of AMIGO2 and 3-phosphoinositide-dependent kinase1 and pharmaceutical compositions, containing the decoy peptide as an active ingredient, for preventing or treating cancer or angiogenesis-related diseases.

BACKGROUND ART

The phosphoinositide 3-kinase (PI3K)/3-phospho-inositide-dependent kinase 1 (PDK1)/protein kinase B (Akt) signaling pathway plays vital roles in the transduction of extracellular cues that control multiple aspects of biological processes, including cell growth, survival, protein translation, metabolism, and angiogenesis. Dysregulation of this pathway is also thought to be correlated with the pathogenesis of many human diseases including cancer, as well as metabolic, cardiovascular, and neurological disorders (Chang et al., 2010; Dimmeler and Zeiher, 2000a; Portt et al., 2011; Raff, 1992; Thompson, 1995; Toker and Newton, 2000). Numerous studies illustrate that abnormal activation of the Akt pathway is one of the principal causative factors for the onset and progression of human cancers (Vivanco and Sawyers, 2002). Oncogenic mutations of Akt pathway regulators such as PI3K, PTEN, and PDK1 were commonly detected in many types of cancers in the breast, endometrium, prostate, liver, lung, brain and skin (Raimondi and Falasca, 2011; Sheppard et al., 2012). The Akt pathway is involved in tumor angiogenesis and the epithelial to mesenchymal transition process, which play essential roles in cancer metastasis and the generation of cancer stem cells (Chang et al., 2013; Sheppard et al., 2012). Moreover, Akt serves as a crucial downstream mediator of angiogenic ligands in endothelial cells (ECs) including VEGF, and coordinates diverse aspects of vascular functionality including EC survival, proliferation, migration, permeability, vascular tone, and angiogenesis (Dimmeler and Zeiher, 2000b; Liu et al., 2000; Vicent et al., 2003). Thus, the regulators of the PI3K/Akt pathway have become attractive targets for cancer prevention and chemotherapy. Currently, diverse classes of PI3K/Akt pathway inhibitors are being assessed for cancer-related clinical trials.

In general, the PI3K/Akt pathway is triggered by multiple stimuli such as growth factors, cytokines, cell to cell junctions, and the ECM (Bischoff, 1995; Dimmeler and Zeiher, 2000b; Lamalice et al., 2007; Strømblad and Cheresh, 1996). Once PI3K signaling is activated by a stimulus, phosphatidylinositol-(3,4,5)-triphosphate (PIP3), a product of PI3K, recruits the pleckstrin homology (PH) domain of PDK1 to the plasma membrane, which results in activation of membrane associated Akt at Thr308 (Datta et al., 1999; Lim et al., 2003; Mora et al., 2004; Pearce et al., 2010; Primo et al., 2007). Alternatively, when PIP3-induced Akt conformation changes occur prior to Thr308 phosphorylation by PDK1, conformational changes that permit Ser473 phosphorylation by mammalian target of rapamycin complex 2 can likewise occur. However, Akt phosphorylation at Ser473 also occurred by mammalian target of rapamycin complex 2 (mTOR2) independently of PIP3 (Huang et al., 2011; King et al., 1997). In addition, PIP3 binding activates PDK1 by promoting Ser241 autophosphorylation (Gao and Harris, 2006). The mutation of PDK1 at the Ser241 residue causes a significant reduction in PDK1 activity towards Akt (Casamayor et al., 1999). However, the additional mechanisms of PDK1 localization to the plasma membrane following Akt activation require further clarification.

Throughout the entire specification, many papers and patent documents are referenced and their citations are represented. The disclosure of cited papers and patent documents are entirely incorporated by reference into the present specification, and the level of the technical field within which the present invention falls, and details of the present invention are explained more clearly.

DETAILED DESCRIPTION OF THE INVENTION

Technical Problem

The present inventors have endeavored to develop novel pharmaceutical compositions capable of effectively preventing or treating cancer and angiogenesis-related diseases. As a result, the present inventors have verified that a decrease in the expression of the adhesion molecule with Ig-like domain 2 (AMIGO2) gene or the treatment of a decoy peptide having the sequence of amino acid residues 465-474 of the AMIGO2 sequence, which is contained in the cytosolic domain (CD) of AMIGO2, induces apoptosis of vascular endothelial cells; reduces migration and adhesion of the endothelial cells; causes defects in vascular induction, survival, and growth, and that these effects result from the inhibition of Akt signaling caused by the inhibition of a direct interaction of the cytosolic domain of AMIGO2 and the PH domain of PDK1, and thus the present inventors have completed the present invention.

Therefore, an aspect of the present invention is to provide a decoy peptide or polypeptide, which inhibits the binding of AMIGO2 and 3-phosphoinositide-dependent kinase 1 (PDK1).

Another aspect of the present invention is to provide a pharmaceutical composition, containing the decoy peptide of the present invention, for preventing or treating cancer or an angiogenic disease.

Still another aspect of the present invention is to provide a method for screening a material for preventing or treating cancer or an angiogenic disease.

Still another aspect of the present invention is to provide a pharmaceutical composition for preventing or treating cancer or an angiogenic disease, the composition containing, as an active ingredient, an AMIGO2 gene expression inhibitor or an AMIGO2 activity inhibitor.

Other purposes and advantages of the present disclosure will become more obvious with the following detailed description of the invention, claims, and drawings.

Technical Solution

In accordance with an aspect of the present invention, there is provided a decoy peptide or polypeptide containing the sequence of amino acid residues 465-474 of SEQ ID NO: 1, wherein the decoy peptide or polypeptide inhibits the binding of adhesion molecule with Ig-like domain 2 (AMIGO2) and 3-phosphoinositide-dependent kinase 1 by competitive inhibition.

The present inventors have endeavored to develop novel pharmaceutical compositions capable of effectively preventing or treating cancer and angiogenesis-related diseases. As a result, the present inventors have verified that a decrease in the expression of the adhesion molecule with Ig-like domain 2 (AMIGO2) gene or the treatment of a decoy peptide having the sequence of amino acid residues 465-474 of the AMIGO2 sequence, which is contained in the cytosolic domain of AMIGO2, induces apoptosis of vascular endothelial cells; reduces migration and adhesion of the endothelial cells; causes defects in vascular induction, survival, and growth, and that these effects result from the inhibition of Akt signaling caused by the inhibition of a direct interaction of the cytosolic domain of AMIGO2 and the PH domain of PDK1.

The decoy peptide or polypeptide of the present invention contains the sequence of amino acid residues 465-474 of SEQ ID NO: 1. In the decoy peptide or polypeptide, the sequence of amino acid residues 465-474 of SEQ ID NO: 1 is essential in an action and function of the decoy peptide or polypeptide to inhibit the binding of AMIGO2 and PDK1. In this sense, the decoy peptide or polypeptide of the present invention includes any peptide or polypeptide containing the sequence of amino acid residues 465-474 of SEQ ID NO: 1 so long as the function or activity as a decoy on AMIGO2 is maintained.

As used herein, the term "peptide" refers to a linear molecule formed by binding amino acid residues to each other via peptide bonds. As used herein, the term "polypeptide" refers to a polymer of (the same or different) amino acids bound to each other via peptide bonds.

The term used herein "decoy peptide or polypeptide" in conjunction with AMIGO2 is a peptide or polypeptide that is designed to contain a partial peptide sequence in the cytosolic domain of AMIGO2, and the decoy peptide or polypeptide can block the action of PDK1 by binding to PDK1 in a competitive manner.

The term "competitive inhibition" used herein with reference to the decoy peptide (or polypeptide) refers to an inhibition of the binding of AMIGO2 and PDK1 by competitive binding to PDK1. The decoy peptide or polypeptide binds to PDK1 in such a manner that it competes with the cytosolic domain of AMIGO2, which binds to the PH domain of PDK1.

According to an embodiment of the present invention, the decoy peptide or polypeptide of the present invention is a cytoplasmic peptide or polypeptide. That is, the decoy peptide or polypeptide of the present invention does not contain an amino acid domain that may hinder the decoy peptide or polypeptide from being located in the cytoplasm. For example, the amino acid domain includes a membrane-spanning domain and an organelle-targeting domain, but is not limited thereto. In this regard, the decoy peptide or polypeptide of the present invention may contain any amino acid residue so long as the decoy peptide or polypeptide can be located in the cytoplasm.

The decoy peptide or polypeptide of the present invention contains a decoy peptide or polypeptide with any length so long as the binding of AMIGO2 and PDK1 is inhibited.

According to an embodiment of the present invention, the decoy peptide or polypeptide of the present invention further contains 0-50, 0-40, 0-30, 0-20, 0-10, 0-3, or 2 amino acid residues in an N-terminal direction of the sequence of amino acid residues 465-474 of SEQ ID NO: 1, and 0-50, 0-40, 0-30, 0-20, 0-10, 0-3, or 2 amino acid residues in a C-terminal direction thereof. As validated in the examples below, the amino acid residues in an N-terminal or C-terminal direction of the sequence of amino acid residues 465-474 of SEQ ID NO: 1 are not amino acids that are essential to inhibit the binding AMIGO2 and PDK1, which is the feature of the present invention, but may prevent peptide ubiquitination to improve stability (N-end rule) and help keep a three-dimensional structure of the peptide.

The decoy peptide or polypeptide of the present invention may include a peptide or polypeptide having one or more amino acid residues with a modified side chain. Examples of the side chain modification include modifications of amino groups, such as, reductive alkylation; amidination with methylacetimidate; acylation with acetic anhydride; carbamolyation of amino groups with cyanate; trinitrobenzylation of amino acid with 2,4,6-trinitrobenzene sulfonic acid (TNBS); alkylation of amino groups with succinic anhydride; and pyridoxylation with pyridoxal-5-phosphate followed by reduction with NaBH4.

The guanidine group of the arginine residue may be modified by the formation of a heterocyclic condensate using a reagent, such as 2,3-butanedione, phenylglyoxal, and glyoxal. The carboxyl group may be modified by carbodiimide activation via O-acylisourea formation, followed by subsequent derivatization, for example, to a corresponding amide.

The sulfhydryl group may be modified by methods, such as carboxymethylation with iodoacetic acid or iodoacetamide; performic acid oxidation with cysteic acid; formation of mixed disulfides by other thiol compounds; a reaction by maleimide, maleic anhydride, or other substituted maleimide; formation of mercury derivatives using 4-chloromercuribenzoate, 4-chloromercuriphenylsulfonic acid, phenylmercury chloride, 2-chloromercuri-4-nitrophenol, and other mercurial agents; and carbamolyation with cyanate at alkaline pH. Any modification of the cysteine residue should not affect the formation of a disulfide bond, which is required by the peptide. In addition, the sulfhydryl group of cysteine may be substituted with a selenium equivalent, whereby a diselenium bond may be formed instead of at least one disulfide bonding site in the peptide.

The tryptophan residue may be modified by, for example, oxidation with N-bromosuccinimide or alkylation of the indole ring by 2-hydroxy-5-nitrobenzyl bromide or sulfonyl halide. Meanwhile, the tyrosine residue may be modified by nitration using tetranitromethane to form a 3-nitrotyrosine derivative.

The modification of the imidazole ring of the histidine residue may be accomplished by alkylation with an iodoacetic acid derivative or N-carbethoxylation with diethylpyrocarbonate.

The proline residue may be modified by, for example, hydroxylation at the 4-position.

The decoy peptide or polypeptide of the present invention can have further improved stability by modifying amino acid residues thereof. For example, at least one amino acid residue of the decoy peptide or polypeptide of the present invention has an acetyl group, a fluorenylmethoxy carbonyl group, a formyl group, a palmitoyl group, a myristyl group, a stearyl group, or polyethylene glycol. According to an embodiment of the present invention, an acetyl protective group is bound to the decoy peptide or polypeptide of the present invention.

As used herein, the term "stability" refers to storage stability (e.g., room-temperature stability) as well as in vivo stability. The foregoing protective group protects the peptide of the present invention from the attack of protein cleavage enzymes in vivo.

According to an embodiment of the present invention, a cell penetrating peptide is further bound to the decoy peptide or polypeptide of the present invention. According to another embodiment of the present invention, a cell penetrating peptide is further bound to the N-terminal and/or the C-terminal of the decoy peptide or polypeptide of the present invention.

In order to deliver the decoy peptide or polypeptide of the present invention into endothelial cells, the decoy peptide or polypeptide needs to contain a cell penetrating peptide. As used herein, the term "cell penetrating peptide" refers to a peptide necessary to deliver a specific peptide (or polypeptide) into a cell. The cell penetrating peptide normally contains sequences of 10-50 or more amino acid residues.

The cell penetrating peptide has an amino acid sequence per se capable of penetrating the phospholipid bilayer of the cell membrane, and includes, for example, a Tat-derived peptide, a signal peptide (e.g., a cell penetrating peptide), an arginine-rich peptide, a transportan, or an amphiphathic peptide carrier, but is not limited thereto (Morris, M. C. et al., *Nature Biotechnol.* 19:1173-1176 (2001); Dupont, A. J. and Prochiantz, A., CRC Handbook on Cell Penetrating Peptides, Langel, Editor, CRC Press, (2002); Chaloin, L. et al., *Biochemistry* 36(37):11179-87 (1997); and Lundberg, P. and Langel, U., *J. Mol. Recognit.* 16(5):227-233 (2003)). In addition to these naturally occurring peptides, various antennapedia-based peptides are well known to have a cell penetrating property and contain retro-inverso and D-isomer peptides. (Brugidou, J. et al., *Biochem Biophys Res Commun.* 214(2):685-93 (1995); Derossi, D. et al., *Trends Cell Biol.* 8:84-87 (1998)).

According to another embodiment of the present invention, the cell penetrating peptide of the present invention contains the amino acid sequence of SEQ ID NO: 3. According to a specific embodiment of the present invention, the cell penetrating peptide of the present invention consist of the amino acid sequence of SEQ ID NO: 3.

In addition, the decoy peptide or polypeptide of the present invention may contain another fusion protein for easy purification, and examples of the fusion protein include glutathione S-transferase (Pharmacia, USA), maltose binding protein (NEB, USA), FLAG (IBI, USA), and 6×His (hexahistidine; Quiagen, USA), but are not limited thereto. According to an embodiment of the present invention, the fusion protein of the present invention is purified by affinity chromatography. For example, the fusion of the glutathione S-transferase allows the use of glutathione, which is a substrate therefor, and the Ni-NTA His-binding resin column (Novagen, USA) is employed for 6×His, thereby promptly and easily obtaining fusion proteins.

According to an embodiment of the present invention, AMIGO2 of the present invention is derived from a human being, and the amino acid sequence thereof is disclosed in the National Center for Biotechnology Information (NCBI). The accession number of the human AMIGO2 amino acid sequence in NCBI is AAH95477.1.

According to the present invention, the term "decoy peptide or polypeptide" is construed to include functional equivalents of the decoy peptide or polypeptide of the present invention. As used herein, the term "functional equivalents" refers to amino acid sequence variants having an amino acid substitution, addition, or deletion in some of the amino acid sequence of the decoy peptide or polypeptide while simultaneously having similar or improved biological activity, compared with the decoy peptide or polypeptide of the present invention. The amino acid substitution may be a conservative substitution. Examples of the naturally occurring amino acid conservative substitution include aliphatic amino acids (Gly, Ala, and Pro), hydrophobic amino acids (Ile, Leu, and Val), aromatic amino acids (Phe, Tyr, and Trp), acidic amino acids (Asp and Glu), basic amino acids (His, Lys, Arg, Gln, and Asn), and sulfur-containing amino acids (Cys and Met). The amino acid deletion is located in a region that is not directly involved in the activity of the decoy peptide and polypeptide of the present invention.

According to the present invention, the amino acid sequence of the decoy peptide and polypeptide usable in the present invention is construed to include a peptide sequence that has substantial identity to the sequence of the decoy peptide of the present invention. As used herein, the term "substantial identity" means that two amino acid sequences, when optimally aligned and then analyzed by an algorithm normally used in the art, such as BLAST, GAP, or BESTFIT, or by visual inspection, share at least about 60%, 70%, 80%, 85%, 90%, or 95% sequence identity. Methods of alignment for sequence comparison are known in the art. Various methods and algorithms for alignement are disclosed in Smith and Waterman, *Adv. Appl. Math.* 2:482 (1981); Needleman and Wunsch, *J. Mol. Bio.* 48:443 (1970); Pearson and Lipman, Methods in Mol. Biol. 24: 307-31 (1988); Higgins and Sharp, *Gene* 73:237-44 (1988); Higgins and Sharp, *CABIOS* 5 151-3 (1989); Corpet et al., *Nuc. Acids Res.* 16:10881-90 (1988); and Huang et al., *Comp. Appl. BioSci.* 8:155-65 (1992) and Pearson et al., *Meth. Mol. Biol.* 24:307-31 (1994).

The NCBI Basic Local Alignment Search Tool (BLAST, Altschul et al., J. Mol. Biol. 215:403-10(1990)) is available from the National Center for Biological Information (NCBI), and on the Internet, for use in connection with the sequence analysis programs blastp, blasm, blastx, tblastn and tblastx. BLAST can be accessed at www.ncbi.nlm.nih-.gov/BLASTL/. A description of how to determine sequence identity using this program is available at www.ncbi.nlm-.nih.gov/BLAST/blast_help.html.

According to an embodiment of the present invention, the decoy peptide or polypeptide of the present invention inhibits the binding of the cytoplasm domain of AMIGO2 and the pleckstrin homology (PH) domain of PDK1.

According to another embodiment of the present invention, the decoy peptide or polypeptide of the present invention inhibits the binding of the sequence of amino acid residues 465-474 in the AMIGO2 amino acid sequence and the pleckstrin homology (PH) domain of PDK1.

In accordance with another aspect of the present invention, there is provided a pharmaceutical composition for preventing or treating cancer or an angiogenic disease, the pharmaceutical composition containing: (a) a pharmaceutically effective amount of the decoy peptide or polypeptide of the present invention; and (b) a pharmaceutically acceptable carrier.

As used with respect to cancer or an angiogenic disease, the term "preventing" refers to the complete prevention of cancer or an angiogenic disease, the prevention of the occurrence of symptoms in a subject with the disease or the prevention of a recurrence of symptoms in a subject with the disease.

As used with respect to cancer or an angiogenic disease, the term "treating" refers to the removal of some or all symptoms or the reduction of the severity of symptoms of cancer or an angiogenic disease in a subject.

As used with respect to cancer or an angiogenic disease, the term "pharmaceutically effective amount" refers to an amount that is sufficient to prevent or treat symptoms, conditions, or disorders of cancer or an angiogenic disease.

As used herein, the term "subject" includes humans, non-human mammals, or animals. The term "non-human mammals" means domestic animals and companion animals, such as cattle, sheep, goats, equines, swine, dogs, and cats.

According to the present invention, the pharmaceutical composition containing the decoy peptide or polypeptide of the present invention as an active ingredient may be used in the prevention or treatment of cancer or an angiogenic disease.

The decoy peptide or polypeptide of the present invention induces apoptosis of endothelial cells and thus is effective in the prevention or treatment of cancer; reduces migration and adhesion of endothelial cells; and effectively inhibits angiogenesis through the mechanism causing defects in vascular induction, survival, and growth, and thus the decoy peptide or polypeptide is very effective in the prevention or treatment of an angiogenic disease. The angiogenic disease means a disease caused by the formation of blood vessels, and examples thereof may include cancer, diabetic retinopathy, retinopathy of prematurity, corneal graft rejection, neovascular glaucoma, erythema, proliferative retinopathy, psoriasis, hemophiliac joints, capillary proliferation within atherosclerotic plaques, keloid, wound granulation, vascular adhesions, rheumatoid arthritis, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, inflammation, and neurodegenerative diseases, but are not essentially limited thereto.

According to an embodiment of the present invention, the angiogenic disease of the present invention is selected from the group consisting of diabetic retinopathy, retinopathy of prematurity, corneal graft rejection, neovascular glaucoma, erythema, proliferative retinopathy, psoriasis, hemophiliac joints, capillary proliferation within atherosclerotic plaques, keloid, wound granulation, vascular adhesions, rheumatoid arthritis, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, inflammation, and neurodegenerative diseases. According to an embodiment of the present invention, the angiogenic disease is selected from the group consisting of diabetic retinopathy, retinopathy of prematurity, and proliferative retinopathy.

According to the present invention, the pharmaceutical composition of the present invention may contain a pharmaceutically acceptable carrier. The pharmaceutically acceptable carrier contained in the pharmaceutical composition of the present invention is typically used at the time of preparation, and examples thereof include carbohydrate-based compounds (e.g., lactose, amylose, dextrose, sucrose, sorbitol, mannitol, starch, cellulose, etc.), acacia gum, calcium phosphate, alginate, gelatin, calcium silicate, microcrystalline cellulose, polyvinylpyrrolidone, cellulose, water, syrup, a salt solution, alcohol, arabic gum, vegetable oils (e.g., corn oil, cotton seed oil, soybean oil, olive oil, coconut oil, etc.), polyethylene glycol, methyl cellulose, methylhydroxybenzoate, propylhydroxybenzoate, talc, magnesium stearate, and mineral oils, but are not limited thereto. The pharmaceutical composition of the present invention may further contain, in addition to the above ingredient, a lubricant, a wetting agent, a sweetening agent, a flavoring agent, an emulsifier, a suspending agent, a preservative, and the like. Suitable pharmaceutically acceptable carriers and preparations are described in detail in *Remington's Pharmaceutical Sciences* (19th ed., 1995).

The pharmaceutical composition of the present invention may be administered orally or parenterally, and in the case of parenteral administration, intravenous injection, subcutaneous injection, muscle injection, or the like may be employed.

The appropriate dose of the pharmaceutical composition of the present invention varies depending on factors, such as the formulating method, manner of administration manner, patient's age, body weight, gender, morbidity, food, time of administration, route of administration, excretion rate, and response sensitivity, and the ordinarily skilled practitioner can easily determine and prescribe the dose that is effective for the desired treatment or prevention. According to a preferred embodiment of the present invention, the appropriate dose per day is 0.0001~100 mg/kg (body weight). The dosage may be administered once a day or divided into multiple doses.

The pharmaceutical composition of the present invention may be formulated into a unit dosage form or may be prepared in a multi-dose container by using a pharmaceutically acceptable carrier and/or excipient according to the method easily conducted by a person having an ordinary skill in the art to which the present invention pertains. Here, the dosage form may be a solution in an oily or aqueous medium, a suspension, an emulsion, an extract, a powder, granules, a tablet, or a capsule, and may further contain a dispersant or a stabilizer.

In accordance with another aspect of the present invention, there is provided a method for preventing or treating cancer or an angiogenic disease, the method including:

Administering to a subject in need thereof the above pharmaceutical composition containing (a) a pharmaceutically effective amount of the above decoy peptide or polypeptide; and (b) a pharmaceutically acceptable carrier.

Since the method for preventing or treating cancer or angiogenic diseases shares a target disease and related factors (AMIGO2 and PDK1) with the pharmaceutical composition containing the above-described decoy peptide or polypeptide, descriptions of overlapping contents there between will be omitted to avoid excessive complexity of the present specification.

In accordance with another aspect of the present invention, there is provided a method for screening a material for preventing or treating cancer or an angiogenic disease, the method including:

(a) bringing a test material into contact with cells containing AMIGO2 and 3-phosphoinositide-dependent kinase 1; and (b) investigating the binding of AMIGO2 and 3-phosphoinositide-dependent kinase 1, wherein the test material is determined to be a material for preventing or treating cancer or an angiogenic disease if the test material inhibits the binding of AMIGO2 and 3-phosphoinositide-dependent kinase 1.

The method of the present invention will be described in detail by steps.

Step (a): Bringing Test Material into Contact with Cells Containing AMIGO2 and PDK1

According to the present invention, first, a test material is brought into contact with cells containing AMIGO2 and PDK1

As used herein to recite the screening method of the present invention, the term "test material" refers to an unknown material that is used in screening in order to investigate whether it affects the binding of AMIGO2 and PDK1.

Step (b): Investigating Binding of AMIGO2 and PDK1

After step (a), the binding of AMIGO2 and PDK1 is investigated. If the test material of the present invention inhibits the binding of AMIGO2 and PDK1, the test material may be determined to be a material for preventing or treating cancer or angiogenic diseases.

The binding of AMIGO2 and PDK1 may be determined by various analysis methods. For example, the binding of AMIGO2 and PDK1 can be determined in various immunoassay formats using respective antibodies or labels that specifically bind to AMIGO2 and PDK1.

These immunological analysis methods may be carried out according to various quantitative immunoassay protocols that have been developed in the prior art. Examples of the immunoassay format include radioactive immunoassay, radioactive immunoprecipitation, immunoprecipitation, enzyme-linked immunosorbent assay (ELISA), captured-ELISA, inhibition or competition analysis, sandwich assay, immunofluorescent staining, and immunoaffinity purification, but are not limited thereto. The immunoassay or immuno-staining is disclosed in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, N J, 1984; and Ed Harlow and David Lane, Using Antibodies: A Laboratory Manual, Cold Spring Harbor Laboratory Press, 1999, the contents of which are incorporated herein by reference.

If the signal with respect to the binding of AMIGO2 and PDK1 is weaker in the sample rather than a control sample, the sample is determined to be a candidate material for preventing or treating an angiogenic disease.

Since the method for screening a material for preventing or treating cancer or angiogenic diseases shares a target disease and related factors (AMIGO2 and PDK1) with the pharmaceutical composition containing the above-described decoy peptide or polypeptide, descriptions of overlapping contents there between will be omitted to avoid excessive complexity of the present specification.

Advantageous Effects

Features and advantages of the present invention are summarized as follows:

(a) The present invention provides a decoy peptide or polypeptide capable of inhibiting the binding of AMIGO2 and 3-phosphoinositide-dependent kinase 1 (PDK1), and a pharmaceutical composition, containing the decoy peptide or polypeptide as an active ingredient, for preventing or treating cancer or an angiogenic disease.

(b) The present invention provides a method for screening a material for preventing or treating cancer or an angiogenic disease.

(c) It is worth noting that the decoy peptide or polypeptide of the present invention induces apoptosis through the inhibition of the binding of AMIGO2 and 3-phosphoinositide-dependent kinase 1 (PDK1); reduces migration and adhesion of endothelial cells; significantly reduces vascular induction, survival, and growth.

(d) The decoy peptide or polypeptide of the present invention can contribute to the prevention or treatment of cancer or an angiogenic disease through the inhibition of Akt signaling, resulting from the inhibition of a direct interaction of the cytosolic domain of AMIGO2 and the PH domain of PDK1.

BRIEF DESCRIPTION OF THE DRAWINGS

The patent or application file contains at least one drawing executed in color. Copies of this patent or patent application publication with color drawing(s) will be provided the Office upon request and payment of the necessary fee.

In FIG. 1J to 1N, data were collected from independent experiments and analyzed using a two-tailed unpaired t-test. Data are means±SD.

In FIGS. 2L to 2O, data were collected from mice (n=5) and analyzed using a two-tailed unpaired t-test.

FIG. 5e shows multiple sequence alignments of the AMIGO family CD domains (SEQ ID NOs: 4-6). "*"=the alignment contains identical amino acid residues in all sequences; ":"=the alignment contains different but highly conserved (very similar) amino acids; "."=the alignment contains different amino acids that are somewhat similar; and blank=the alignment contains dissimilar amino acids or gaps (or different bases if DNA sequences are aligned).

FIG. 5f shows a diagram showing the protein sequences of cytosolic-truncated mutants (SEQ ID NO: D. The total length of the cytosolic tail is 103aa.

FIG. 6D shows comparison of cell survival rates between Con without VEGF and PTD-A2 without VEGF (red), and between Con with and without VEGF (blue), and Con with VEGF and PTD-A2 with VEGF (black). In FIGS. 6D and 6E, data were collected from independent experiments and analyzed using a two-tailed unpaired t-test. Data are means±SD.

FIG. 7A shows Photograph of B16F10 melanoma tumors resected after 14 days. Scale bar: 5 mm.

FIG. 7B shows comparisons of tumor volume (n=9 mice per group, 4 mg/kg every other day).

FIGS. 7C and 7F show images (FIG. 7C) and quantification (FIG. 7F) of CD31-positive blood vessels (red) in B16F10 melanoma tumors. DAPI (blue), Scale bar: 100 μm.

FIG. 7D shows images of FITC-Con or A2 (green) in B16F10 melanoma tumors. DAPI (blue); Scale bar: 100 μm.

FIG. 7E shows images of CD31-positive blood vessels (red) and FITC-positive cells (green) in B16F10 melanoma tumors. DAPI (blue); Scale bar: 50 μm.

FIG. 7G shows TUNEL-positive apoptotic cells (red) in tumor section samples. Scale bar: 50 μm. DAPI (blue), * $p<0.05$; *$p<0.005$; ***$p<0.0005$; ns: not significant by the two-tailed Student's t-test.

MODE FOR CARRYING OUT THE INVENTION

Figure 1A:
FIG. 1A shows that AMIGO2 was highly expressed in differentiated ECs. EPC: Endothelial progenitor cells, OEC: out growth endothelial cells.

Hereinafter, the present invention will be described in detail with reference to examples. These examples are only for illustrating the present invention more specifically, and it will be apparent to those skilled in the art that the scope of the present invention is not limited by these examples.

Examples

Materials and Methods

Isolation and Culture of Endothelial Progenitor Cells and ECs

Endothelial progenitor cells (EPC) were isolated from human umbilical cord blood as previously described (Maeng et al., 2009). Briefly, human umbilical cord blood samples (approximately 50 mL each) were collected from fresh placentas with attached umbilical cords by gravity flow. Human umbilical vein endothelial cells (HUVECs) were isolated from human umbilical cord veins using collagenase as described previously (Marin et al., 2001), and cells from passages three to six were used. HUVECs were cultured on 2% gelatin-coated dishes at 37° C. in a 5% $CO_2$-humidified atmosphere using M199 medium (HyClone) containing 20% fetal bovine serum (FBS), 100 U/mL penicillin, 100 μg/mL streptomycin, 3 ng/mL bFGF (Upstate Biotechnology), and 5 U/mL heparin.

Transfection of siRNAs and Plasmids into HUVECs

HUVECs were transfected with scrambled (control) and human AMIGO2 siRNAs using Lipofectamine® (Invitrogen) for 3 h, and cells were assayed 48 h after transfection. Human AMIGO2 siRNA was designed by Invitrogen using the following sequences: 5'-UUAGGAUGCCCUCAGC-UAUCACUGC-3' (SEQ ID NO: 8) and 5'-AUUGUU-GUAAAGCAGAAGCACUUCC-3' (SEQ ID NO: 9). HUVECs were transfected with EGFP-tagged plasmids using Lipofectamine® LTX and PLUS™ (Invitrogen) for 2 h, and cells were assayed 24 h after transfection.

Plasmids

Full-length human AMIGO2 was purchased from GeneCopoeia (Cat No. EX-E1271-M02), and subcloned into the EGFP-tagged vector using HindiIII (5'-CCCAAGCT-TGGCGACCATAATGTCGTTACGTGTACACACT-3' (SEQ ID NO: 10)) and BamH1 (5'-CGGGATCCCGT-TAAGTGGACGCCACAAAAG-3' (SEQ ID NO: 11)). AMIGO2$^{\Delta LRR}$ (40-282aa) was cloned using HindIII, 5'-GATGATGCTGTCAGACCCAGAGGCACCAGG-3' (SEQ ID NO; 12) (megaprimer of signal peptide to IgG domain), 5'-CCTGGTGCCTCTGGGTCTGACAGCAT-CATC-3' (SEQ ID NO: 13) (megaprimer of signal peptide to IgG domain), and BamH1. AMIGO2$^{\Delta IgG}$ (295-381aa) was cloned using HindIII, 5'-GAAATTGCTCACATTGCAAT-TCATAAAGCT-3' (SEQ ID NO: 14) (megaprimer of LRR to transmembrane domain), 5'-AGCTTTATGAATTG-CAATGTGAGCAATTTC-3' (SEQ ID NO: 15) (megaprimer of LRR to transmembrane domain) and BamH1. AMIGO2$^{\Delta CD}$ (Δ420-522aa) was cloned using HindIII (5'-CCCAAGCTTGGCGACCATAATGTCGTTACGTGTA-CACACT-3' (SEQ ID NO: 16)) and BamH1 with a stop codon (5'-CGGGATCCCGTTACAGATAGAGGTA-CAAAA-3' (SEQ ID NO: 17)). AMIGO2$^{CD}$ (420-522aa) was cloned using HindIII (5'-CCCAAGCTTGATGACTC-CATGCCCCTGCAA-3' (SEQ ID NO: 18)) and BamH1 (5'-CGGGATCCCGTTAAGTGGACGCCACAAAAG-3' (SEQ ID NO: 19)). The 491aa and the 457aa constructs were subcloned with BamH1 (5'-CGGGATCCCGTTACACTGC-CTCGCTGGGAAAGA-3' (SEQ ID NO: 20); and 5'-CGGGATCCCGTTATTCATCAGCGGAGGCATCAC-3' (SEQ ID NO: 21), respectively).

EC Adhesion Assay

HUVECs transfected with siRNA were trypsinized and washed twice in phenol-free M199. Prior to seeding, a 96-well plate was coated with 2% gelatin, fibronectin (3 μg/ml in PBS), and collagen type I (10 μg/ml in PBS), and incubated at 37° C. for 1 h in a humidified incubator. Prior to the initiation of the experiments, the wells were rinsed twice with PBS. HUVECs were labeled with calcein AM, and $1.5 \times 10^4$ cells were seeded into each well of the 96-well plates. Cells were incubated for 1 h at 37° C., and non-adherent, calcein-labeled cells were removed by four washes. M199 containing 20% FBS was added to the cells in each well, and the fluorescence was measured (maximum absorbance at 494 nm and maximum emission at 517 nm) using a fluorescein filter set by FLUOstar Omega (BGM LABTECH).

Flow Cytometry Analysis of Apoptosis

Flow cytometry was performed using a FACSCanto™ II flow cytometer (Becton Dickinson). Annexin V-phycoerythrin and 7-amino actinomycin D (7-AAD) staining with an annexin-V-phycoerythrin apoptosis detection kit (BD Pharmingen) were used to identify cells in various stages of apoptosis. HUVECs were transfected and detached using StemPro® Accutase® cell dissociation buffer (Life Technologies) and annexin-V and 7-AAD staining was performed. The annexin-V-phycoerythrin apoptosis detection kit was used to evaluate apoptosis.

EC Migration Assay

The chemotactic motility of HUVECs was assayed in Transwell® chambers (Corning Costar) using polycarbonate filters (8-μm pore size, 6.5-mm diameter). Briefly, the lower surface of the filter was coated with 0.1% gelatin. Fresh M199 medium containing 1% FBS and 20 ng VEGF was added to the lower wells. HUVECs were trypsinized and resuspended in M199 containing 1% FBS to a final concentration of $1 \times 10^6$ cells/mL. A 100 μL aliquot of the cell suspension was added to each of the upper wells and incubated at 37° C. for 4 h. Cells were then fixed and stained with hematoxylin and eosin. Non-migrating cells on the upper surface of the filter were removed by wiping with a cotton swab, and chemotaxis was quantified by counting the cells that migrated to the lower side of the filter using optical microscopy (200× magnification). Ten fields were counted for each assay. Each sample was assayed in triplicate, and the assays were repeated three times.

In Vitro Tube Formation Assay

The tube formation was assayed as previously described (Choi et al., 2009). Briefly, 250 μL of Matrigel™ (BD Biosciences) was added to a 16-mm diameter tissue culture well on the ice. HUVEC cells then ware placed on that and tube formation was confirmed. The images of the tubes were quantified using ImageJ software (National Institutes of Health).

RT-PCR and Real-Time PCR Primers

The human AMIGO2 RT-PCR forward and reverse primers were 5'-GATACTGCAGCAGGGCAGAA-3' (SEQ ID NO: 22) and 5'-GACGCCACAAAAGGTGTGTC-3' (SEQ ID NO: 23), respectively. The forward and reverse murine AMIGO2 primers were 5'-GGCACTTTAGCTCCGT-GATG-3' (SEQ ID NO: 24) and 5'-GTCTCGTTTAACA-GCCGCTG-3' (SEQ ID NO: 25), respectively. For the mouse GAPDH control, the forward and reverse primers were 5'-CAACGACCCCTTCATTGACC-3' (SEQ ID NO: 26) and 5'-AGTGATGGCATGGACTGTGG-3' (SEQ ID NO: 27), respectively. Quantitative real-time PCR was performed in a PikoReal™ Real-Time PCR system (Thermo Scientific).

In Vivo siRNA Injection and Analysis

The sequence 5'-UUGUACAAAAGAUCUCGCUGA-3' (SEQ ID NO: 28) (mouse AMIGO2 siRNA, Dharmacon) was mixed with the TransIT®-QR Starter Kit (Mirus), and subcutaneously injected to each mouse (5 μg/P3.5 mouse) (Behlke, 2006; Bonifazi et al., 2010; Inaba et al., 2012; Mammoto et al., 2009). Hyaloid vessels and retinas were prepared as previously described (Lobov et al., 2005). After 2 days, the differences of protein change, retina, and hyaloid vessels were analyzed.

Immunofluorescence

HUVECs were fixed in 3.7% formaldehyde for 10 min and permeabilized with 0.1% Triton X-100 on the ice. Cells were labeled with anti-FAK antibody (Santa Cruz Biotechnology), anti-PDK1 antibody (Cell Signaling Technology), anti-Akt antibody (Cell Signaling Technology), and anti-AMIGO2 antibody (Abcam) for 2 h at room temperature or overnight at 4° C. Afterwards, the cells were incubated with Alexa 488 and Alexa 546 secondary antibodies (Invitrogen) for 60 min at room temperature, and were then examined under a confocal microscope (LSM 700 META; Carl Zeiss).

Immunoprecipitation

For co-immunoprecipitation, HEK293T cells were lysed in 1 mL lysis buffer (20 mmol/L Tris/HCl pH 8.0, 2 mmol/L EDTA, 137 mmol/L NaCl, 1 mmol/L NaVO$_4$, 1 mmol/L PMSF, 10% glycerol, and 1% Triton X-100), and were centrifuged at 14,000×g for 15 min at 4° C., and then the supernatants were immunoprecipitated with antibodies against FLAG (Sigma-Aldrich) and GFP (Santa Cruz Biotechnology) at 4° C. overnight. The immunoprecipitated proteins were obtained by using protein A-agarose beads (Upstate Biotechnology), and detected by SDS-PAGE.

Preparation of Proteins

GST-CD, 420-484, 420-474, 420-464 and 420-454 were prepared with vector plasmids of pGEX 4T1 and pET32a followed by the preparation of His-PH.BamH1 (5'-CGCG-GATCCGCGGAAAACCTGTATTTTCAGGGCACTC-CATGCCCCTGCAAG-3') (SEQ ID NO: 29) and Xho1 (5'-CCGCTCGAGCGGTCATGATTAAGTGGACGCCA-CAAA-3' (SEQ ID NO: 30), CD; 5'-CCGCTCGAGCGGT-CATGATTACCTGACTTTCCCGTT-3' (SEQ ID NO: 31), 420-484; 5'-CCGCTCGAGCGGTCATGATTAATCCT-TCAGGGGTTC-3' (SEQ ID NO: 32), 420-474; 5'-CCGCTCGAGCGGTCATGATTATTTACCTGCAC-CTGC-3' (SEQ ID NO: 33), 420-464; and 5'-CCGCTC-GAGCGGTCATGATTAGGAGGCATCACTAGC-3' (SEQ ID NO: 34), 420-454) were used, and BamH1 (5'-CGCG-GATCCGGCAGCAACATAGAGCAG-3' (SEQ ID NO: 35)) and Xho1 (5'-CCGCTCGAGCGGTCACTGCACA-GCGGCGTCGGG-3' (SEQ ID NO: 36)) were used for preparing His-PH. The proteins were expressed in *Escherichia coli* BL21, and purified with glutathione-Sepharose 4B resin and Ni2+-NTA-agarose.

Pull-Down Assays

GST and His-fused proteins (1.5 mg/ml:1.5 mg/ml) were incubated for 2 h at 4° C., immobilized on Ni$^{2+}$-NTA resin or glutathione-Sepharose 4B beads, and incubated for 30 min. Proteins were then eluted with elution buffer (25 mM NaPi, 300 mM NaCl, 5 mM β-mercaptoethanol, 500 mM imidazole, pH 7.5), western blot was performed with anti-GST and His antibodies.

Far-Western Analysis

Far-western analysis was performed as previously described (Wu et al., 2007). Briefly, purified GST-tagged proteins (1 μg) were loaded and separated, and then transferred to PVDF membranes. The membranes were denatured and renatured, incubated with purified His-tagged PH domain proteins (10 μg), and then detected with anti-His antibody.

Decoy Peptide Preparation and Treatment

The PTD-A2 of FITC-linker-YGRKKRRQRRR-GKRV-VFLEPLKDTA (SEQ ID NO: 37) (decoy peptide) and the control peptide (FITC-linker-YGRKKRRQRRR-GRVK-TDFLAVPEKL (SEQ ID NO: 38)) (Con-pep) were obtained from Peptron. The experiment was performed using 5 μM concentration in vitro, 4 mg/kg was used for an animal experiment. Peptide treated HUVECs were incubated with serum-free M199 medium at 37° C.

Decoy Peptide Binding and Competition Assays

For the peptide binding assay, the purified His-tagged PH domain proteins were incubated with Ni$^{2+}$-NTA resins for 1 h, incubated in vitro with the FITC-PTD-A2 or Con-pep for 1 h, washed five times, eluted with elution buffer. The FITC level of eluted material was then measured using FLUOstar Omega (BGMLABTECH). For the peptide competition assay, the purified His tagged PH domain proteins were incubated with $Ni^{2+}$-NTA resins for 1 h, incubated in vitro with the Cytoplasm Domain protein of AMIGO2 proteins with FITC-PTD-A2 or Con-pep for 1 h, washed five times, eluted with elution buffer, and the fluorescence was measured. The FITC level of eluted material was then measured using FLUOstar Omega.

Matrigel Plug Angiogenesis Assay

Angiogenesis was evaluated as previously described (Choi et al., 2009). PBS; Matrigel™ (500 μL; BD Biosciences) mixed with PTD-A2 (25 μM), VEGF (200 ng) and heparin (10 U); and Con-pep (25 μM), VEGF (200 ng) and heparin (10 u) were each subcutaneously injected to Five- to six-week-old C57BL/6 mice. Following injection, the Matrigel™ rapidly formed a single, solid gel plug. After five days, the skin of the mouse was pulled back to expose the Matrigel™ plug, which remained intact. To quantify blood vessel formation, hemoglobin was measured using the Drabkin method and the Drabkin reagent kit 525 (Sigma-Aldrich), and immunohistochemistry was performed using anti-CD31 antibody (BD Biosciences) to identify infiltrating ECs.

Mouse Model of OIR

OIR was induced in C57BL/6J mice as previously described (Connor et al., 2009). Briefly, litters of postnatal day seven (P7) C57BL/6J pups were placed in a 75% oxygen atmosphere for five days and then returned to room air at age P12. After returning to room air, the pups were injected with PBS, Con-pep and PTD-A2 every day for five days. Following the injections, crumps of non-vascular regions, vascular regions and blood vessels were detected with CD31 staining.

Tumor Model

B16F10 melanoma cells ($2.5 \times 10^5$ cells in 100 μl) were subcutaneously injected into the dorsal flank of 6-7 week-old mice and then PTD-Con or PTD-A2 peptide (4 mg/kg every other day) was administered by intratumoral injection after the tumor volume exceeded 100 $mm^3$. The size was evaluated every day, tumor samples were frozen sectioned, and stained with anti-CD31 antibody to detect the tumor vascular changes, and then examined the apoptosis bio TUNEL staining. For the TUNEL assay, an in situ cell death detection kit (Roche) was used, and sections were analyzed using a confocal microscope (LSM 700 META; Carl Zeiss).

Statistical Analysis

Data are presented as means±standard deviation (SD). All experiments were performed in triplicate, and representative results are shown.

Results

AMIGO2 Regulates EC Survival, Migration, and Capillary-Like Network Formation Induced by Matrigel.

Figure 1B:
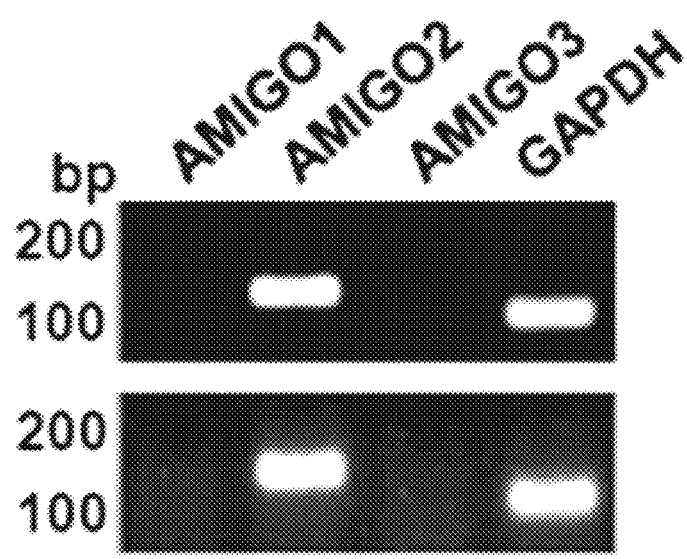
FIG. 1B shows the expression pattern of the AMIGO family that was examined in two different types of HUVECs.
Figure 1C:
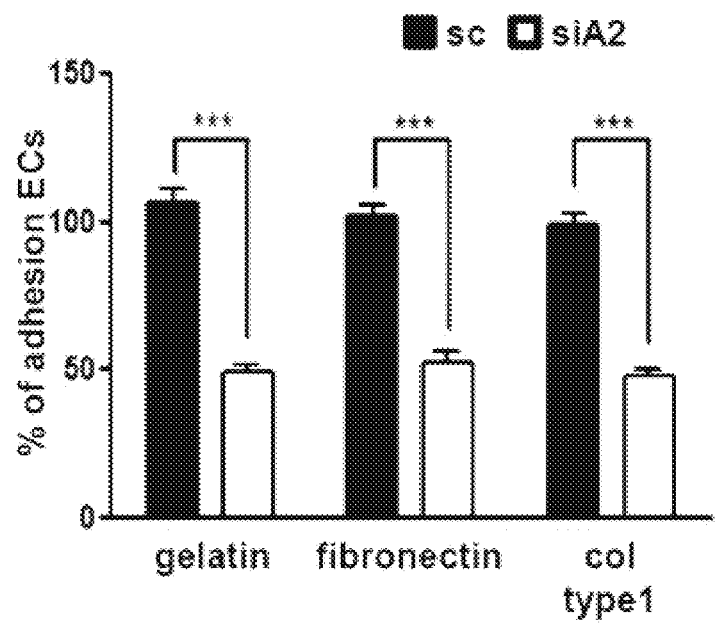
FIG. 1C shows the decrease in EC (gelatin-, fibronectin-, and collagen type 1) adhesion of AMIGO2-depleted HUVECs (n=4; ***p<0.0001).
Figure 1D:
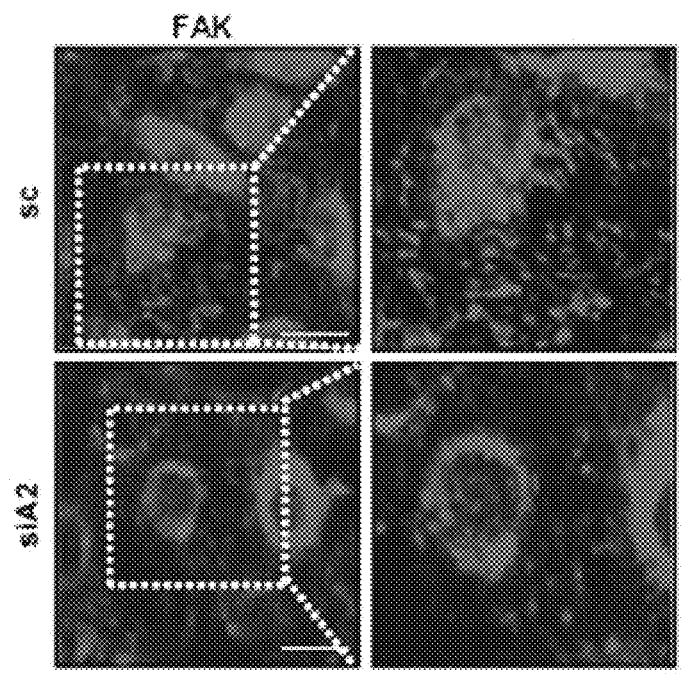
FIG. 1D shows the result of Focal adhesion kinase (FAK) immunostaining. Right images are enlargements of the dotted line-boxed regions in the first column. Sc: control siRNA, siA2: AMIGO2-specific siRNA. Scale bar: 20 µm.
Figure 1E:
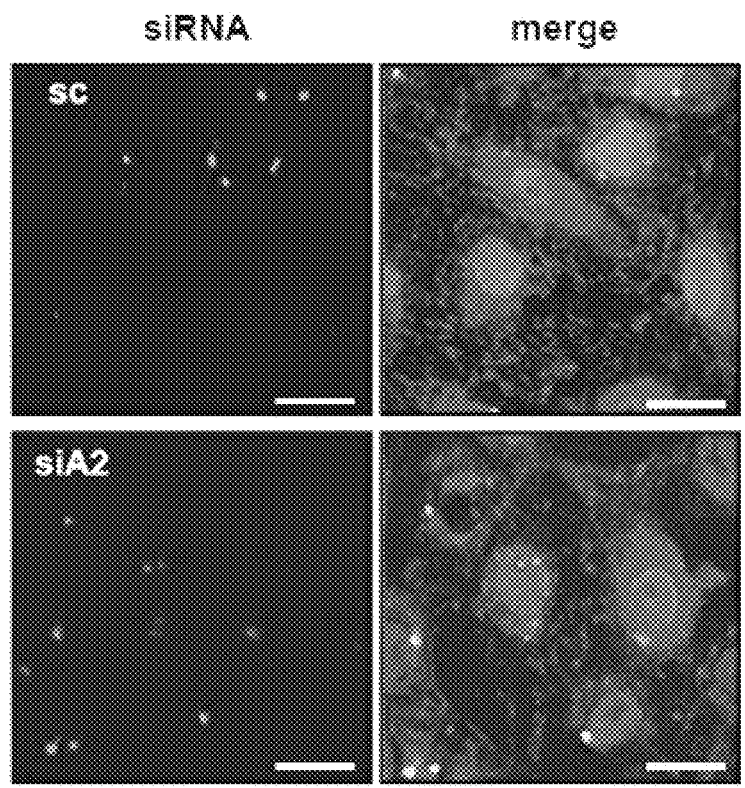
FIG. 1E shows FAK immunostaining that was performed in parallel. FITC-siRNA and merged images of FAK and DAPI were captured. Scale bar: 20 µm.
Figure 1F:
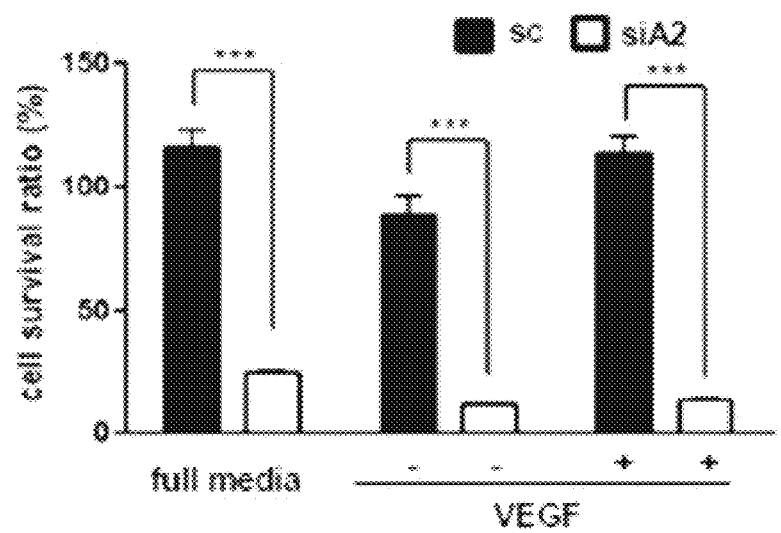
FIG. 1F shows Cell viability of AMIGO2 siRNA-transfected HUVECs in complete media and under conditions of serum-free starvation with or without VEGF (n=6; *** p<0.0001). Data were collected from independent experiments and analyzed using a two-tailed unpaired t-test. Data are means±SD.
Figure 1G:
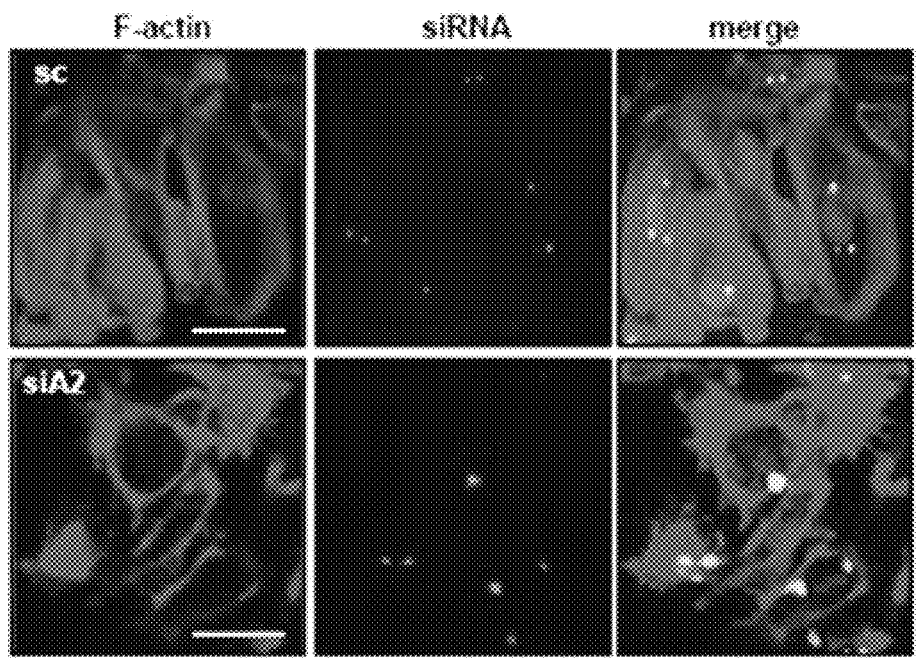
FIG. 1G shows Apoptotic cell shapes that were detected by rhodamine-phalloidin staining for F-actin. Scale bar: 20 µm.
Figure 1H:
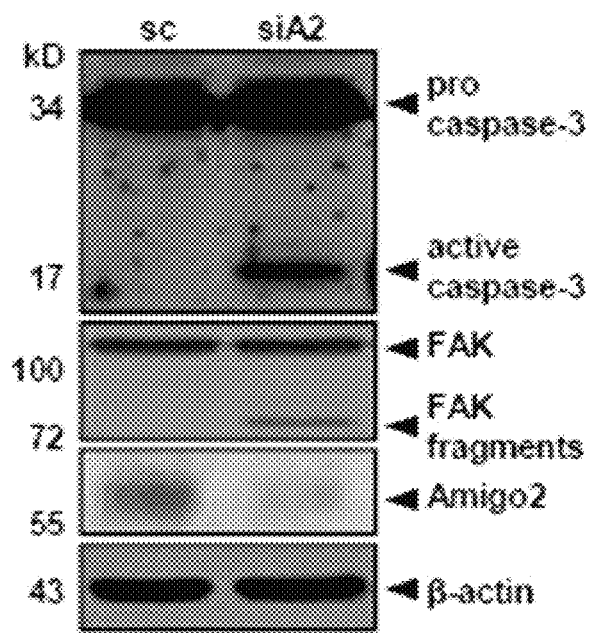
FIG. 1H shows expression of active caspase-3 and FAK fragments in AMIGO2 siRNA transfected ECs.

Affymetrix® gene chip analysis (GEO Accession No. GSE12891) revealed that AMIGO2 is highly expressed in ECs. The higher upregulation of AMIGO2 in ECs than Endothelial Progenitor cells (EPC) was revealed (FIG. 1A). Particularly, it was revealed that AMIGO2 specifically highly expressed in human umbilical vein ECs (HUVECs) among 3 AMIGO family (FIG. 1B). Since AMIGO2 affects cell adhesion and survival in other cell types, we examined these functions in ECs. AMIGO2 siRNA-transfected HUVECs (FIGS. 1C and 1D) displayed reduced adhesion on all three ECM substrates (gelatin, fibronectin, and collagen type I) (FIG. 1C). Immunostaining of FAK revealed low expression of FAK in AMIGO2 siRNA-transfected HUVECs (FIG. 1D and FIG. 1E). In the presence or absence of VEGF, the cell viability of AMIGO2-siRNA transfected HUVECs was decreased (FIG. 1F). AMIGO2-siRNA tranfected HUVECs exhibited F-actin depolymerization, and active caspase-3 and FAK fragments were detected in AMIGO2-knockdown cells (FIGS. 1G and 1H). These are markers of cell apoptosis.

Annexin V-phycoerythrin and 7-amino actinomycin D (7-AAD) staining with an annexin-V phycoerythrin apoptosis detection kit (BD Pharmingen) were used to identify cells in various stages of apoptosis.

Figure 1I:
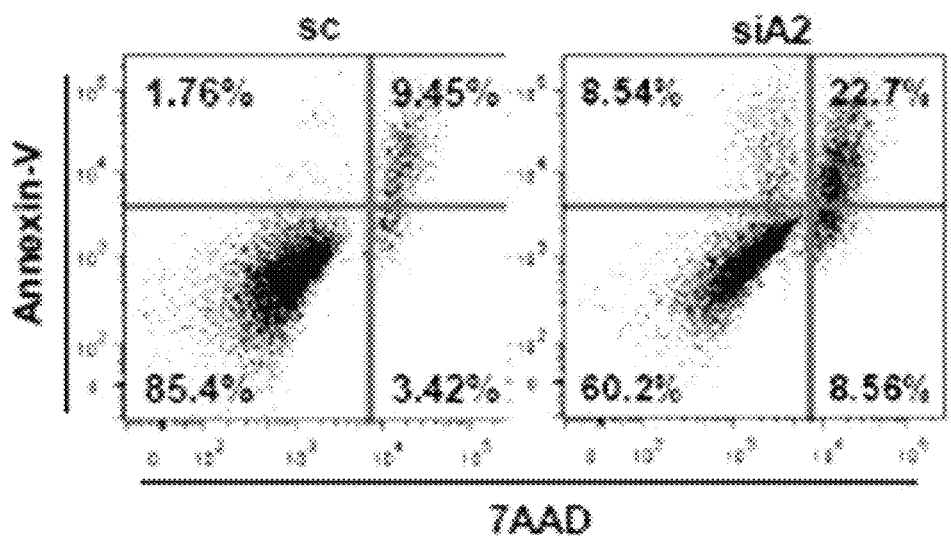
FIG. 1I shows the detection of different stages of apoptosis with phycoerythrin conjugated annexin-V flow cytometry and PerCP-7-AAD staining. Living cells (7AAD−/annexin-V−), early apoptotic cells (7AAD−/annexin-V+), late apoptotic cells (7AAD+/annexin-V+), and necrotic cells (7AAD+/annexin-V−) were used. The data are representative of three experiments conducted using different samples.

Annexin V and 7-amino actinomycin D (7-AAD) labeling was performed, and followed by flow cytometry analysis. As a result, increased levels of apoptosis in AMIGO2-knowdown HUVECs were observed (FIG. 1I).

Figure 1J:
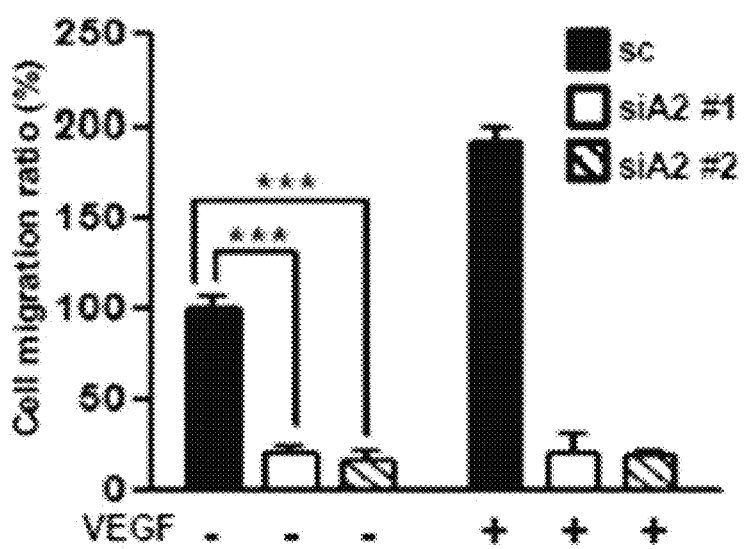
FIGS. 1J and 1K show wound healing migration and gelatin-coated Transwell™ migrations with or without VEGF. Two types of siA2 were evaluated (n=3; * p<0.0001; and n=6; *p<0.0001).
Figure 1K:
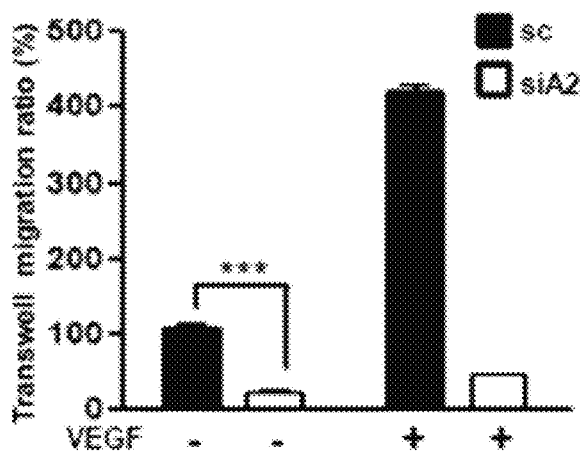
Figure 1L:
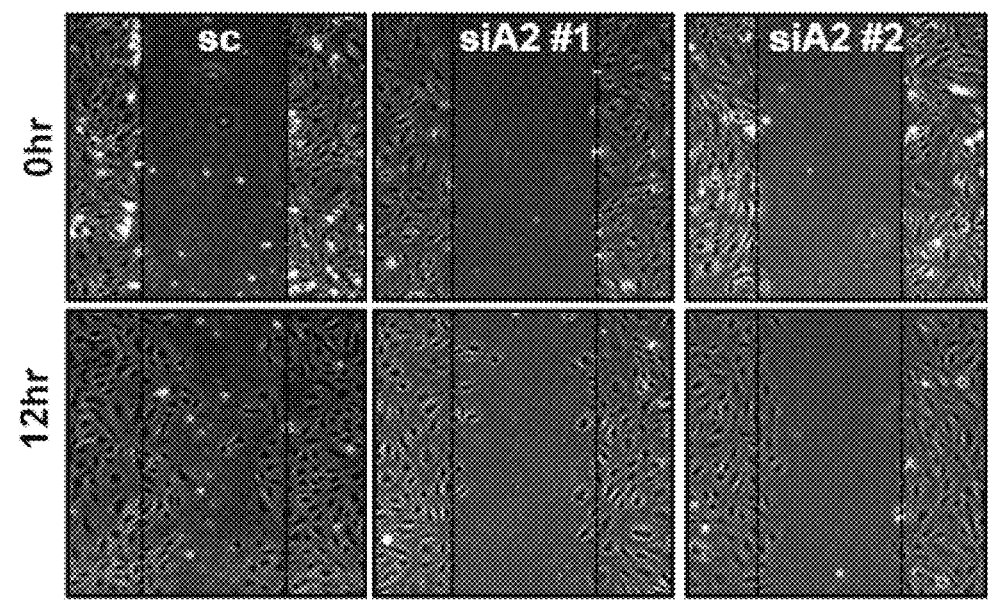
FIG. 1L shows Matrigel™ induced tube-like structure formation. Tube length is presented as the percent of total tube length per field versus untreated control cells (n=4;  p<0.005; * p<0.0005).
Figure 1M:
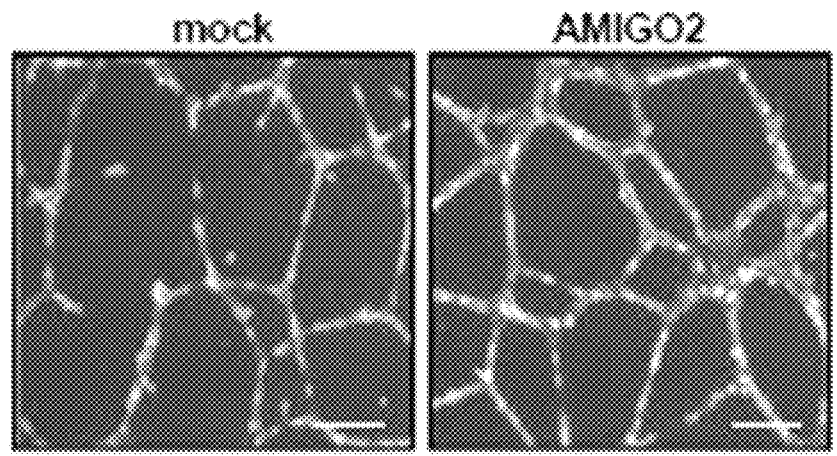
FIGS. 1M and 1N show Matrigel™-induced tube formation by AMIGO2 overexpressed ECs (n=3; *** p<0.0001; ns, not significant). Scale bar, 20 µm.
Figure 1N:
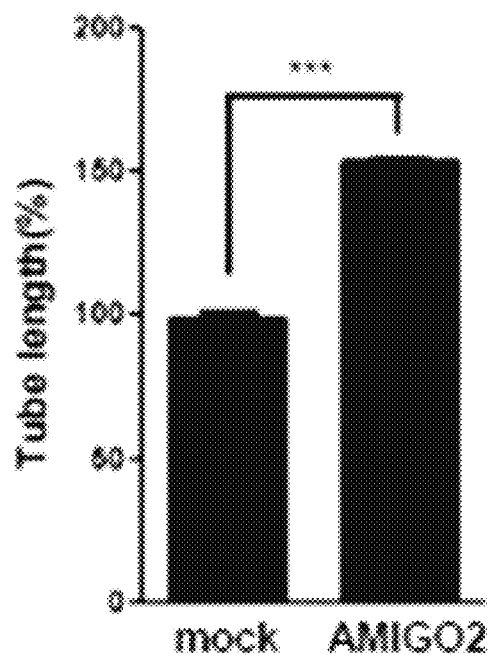
Figure 1O:
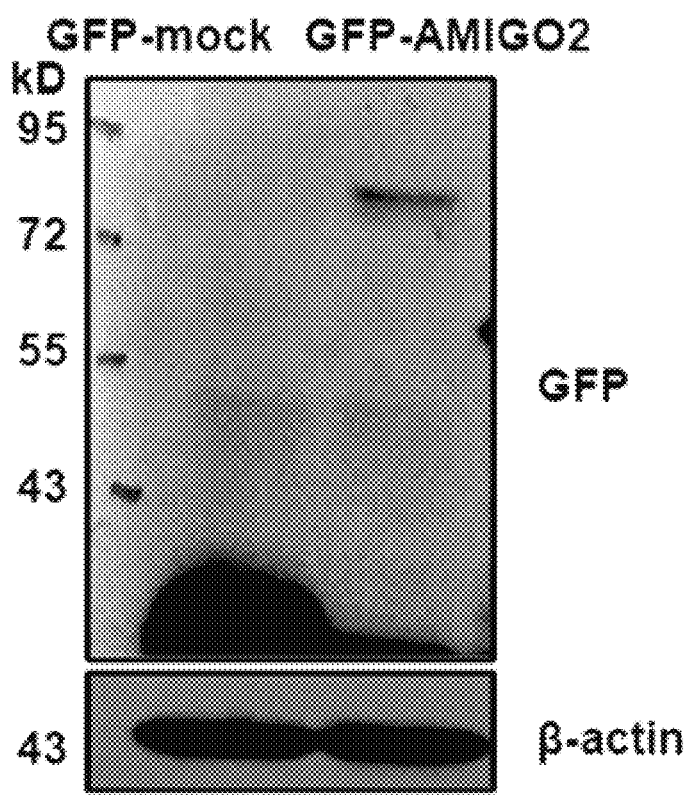
FIG. 1O shows detection of over-expression of AMIGO2 in HUVECs with western blotting.

Further, the additional experiment was performed to reveal the angiogenic function of AMIGO2. By the both wound healing test and chemotactic motility test, the decreased mobility in AMIGO2-knockdown ECs was revealed regardless of VEGF induction (FIG. 1J to 1L). Further, Matrigel™-induced tube formation assay exhibited the reduction of angiogenesis induced by Matrigel and the increase of apoptosis due to decreased adhesion in AMIGO2-knockdown ECs (FIGS. 1M to 1O).

These Results Indicate that AMIGO2 could Modulate Angiogenic Function of ECs.

These results indicate that AMIGO2 could modulate angiogenic function of ECs.

Figure 2A:
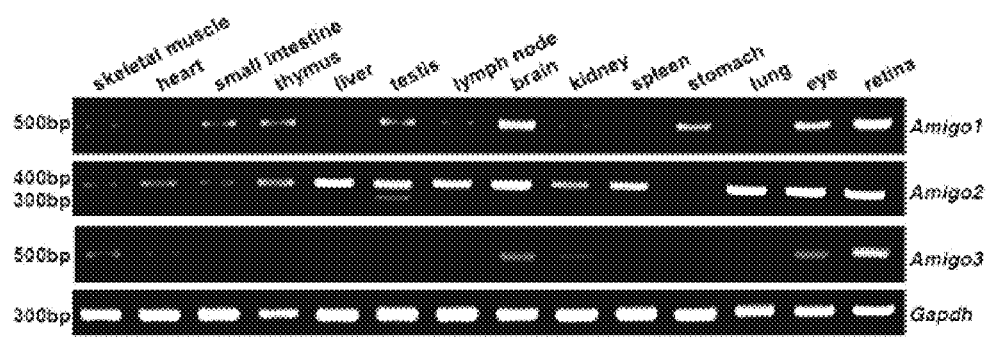
FIG. 2A shows AMIGO family expression pattern verified in adult mouse tissues.

To determine the physiological relevance of AMIGO2 in vivo, we examined expression levels of Amigo family members in mouse. Amigo2 was mainly expressed in the eye, retina, brain, lung, and lymph node (FIG. 2A).

Because the level of Amigo2 expression in the eye was elevated, we investigated the expression of Amigo2 in the hyaloid and retinal vessel systems.

Figure 2B:
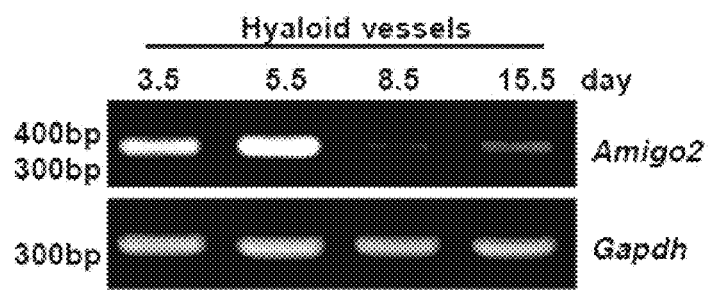
FIGS. 2B and 2D show Amigo2 expression level measured in P3.5-15.5 mouse hyaloid vessels and retinas by RT-PCR.
Figure 2C:
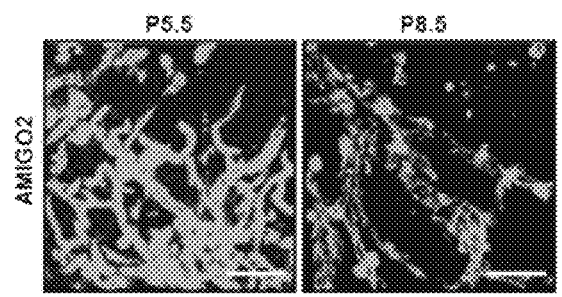
FIG. 2C shows AMIGO2 in hyaloids vessels at P5.5 and 8.5. Scale bar: 50 µm.
Figure 2D:
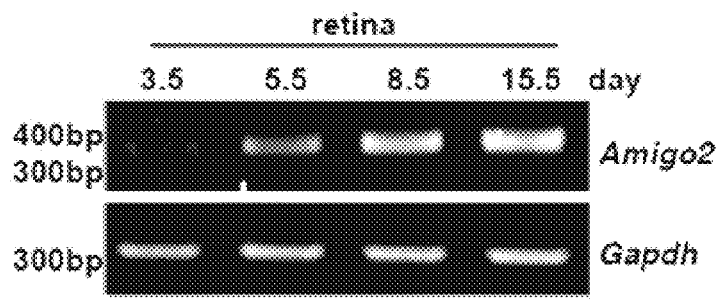
Figure 2E:
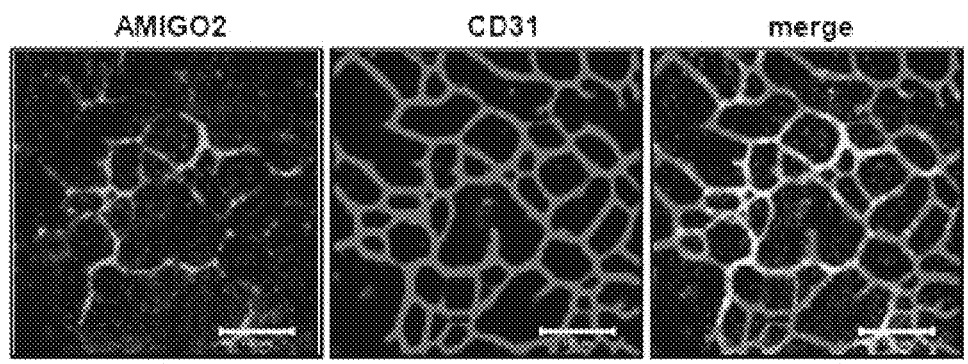
FIG. 2E shows immunostaining images of AMIGO2 (green), CD31 (endothelial cell marker; red), and AMIGO2/CD31 merged color in retinal vessels at P11.5. Scale bar: 100 µm.
Figure 2F:
FIGS. 2F and 2G show that AMIGO2-specific in vivo siRNA was selected and validated in mouse tissues.
Figure 2G:
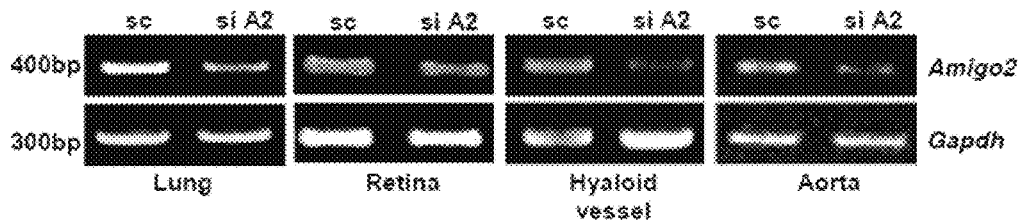
Figure 2H:
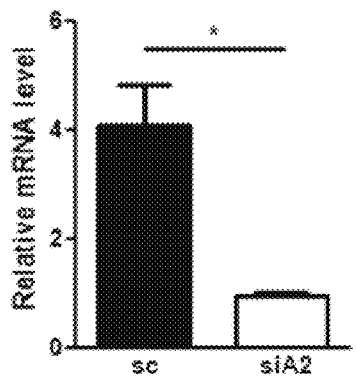
FIG. 2H shows real-time PCR confirming AMIGO2 knockdown in hyaloid vessels.

In hyaloid vessels, AMIGO2 was detectable from postnatal day 3.5 (P3.5), with the highest expression at P5.5, after which expression decreased (FIGS. 2B and 2C). In retinal vessels, AMIGO2 was detected at P5.5 and consistently increased in retinal vessels over time (FIGS. 2D and 2E).

Figure 2I:
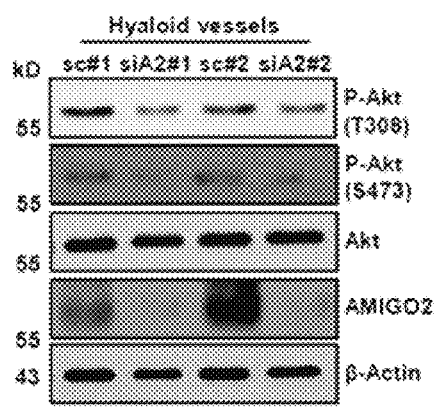
FIGS. 2I and 2J show Akt phosphorylation in hyaloid vessels and retinas from Amigo2-depleted mice. The data are representative of six mice.
Figure 2J:
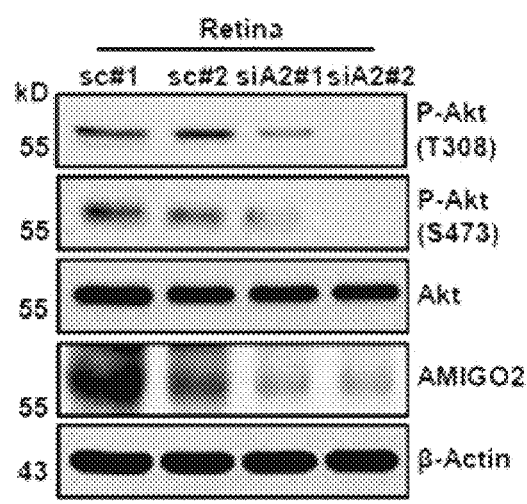
Figure 2K:
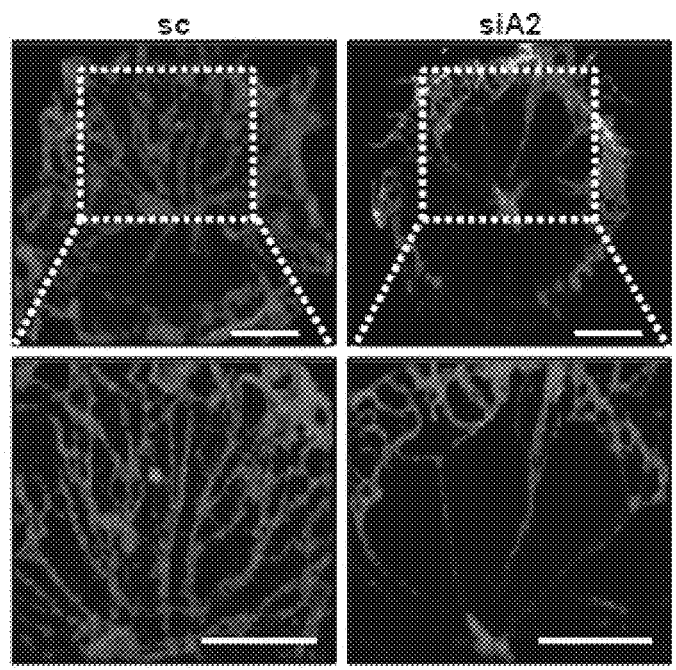
FIG. 2K shows impairment of hyaloid vessel structures in Amigo2 siRNA-injected mice. Scale bars: 200 µm.
Figure 2L:
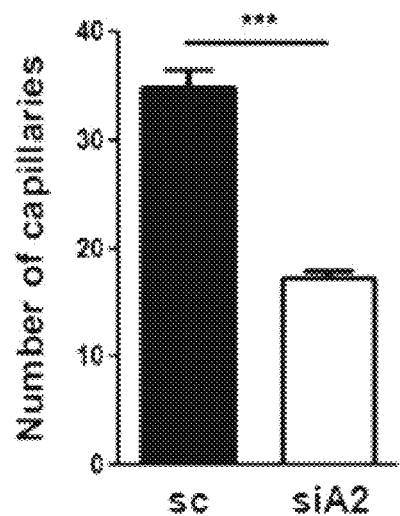
FIG. 2L shows capillary quantification (n 5; *** p<0.0001; data are means±SD).
Figure 2M:
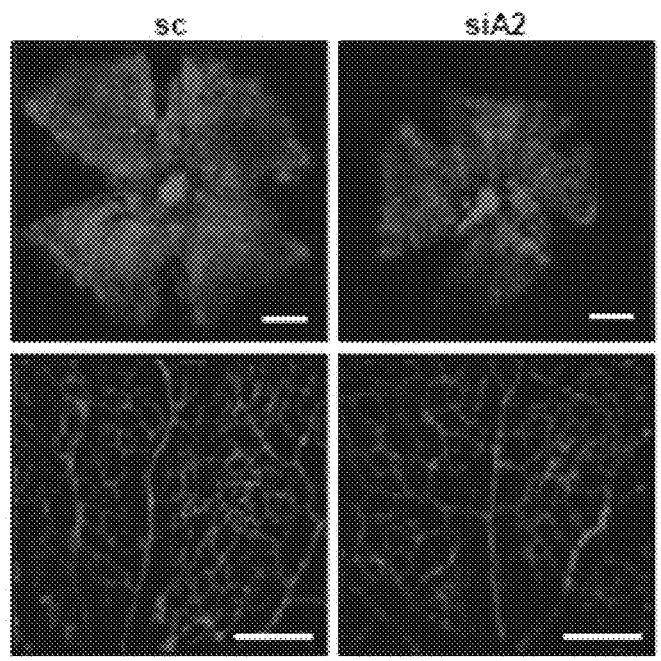
FIG. 2M shows visualization of blood vessels by iB4-staining of Amigo2-depleted retinas from P5.5 mice. Scale bars: 200 µm.
Figure 2N:
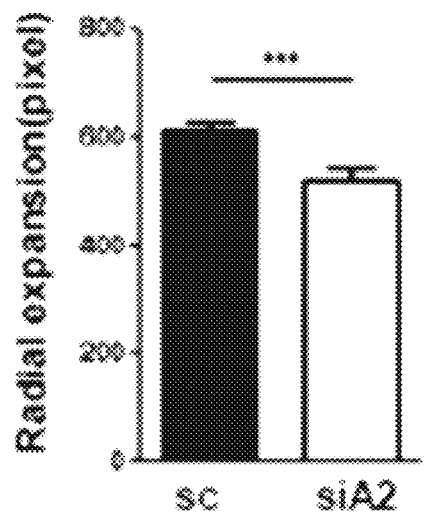
FIGS. 2N and 2O show quantification of radial expansions and retinal vascular areas (n=5; ** p<0.005; data are means±SD).
Figure 2O:
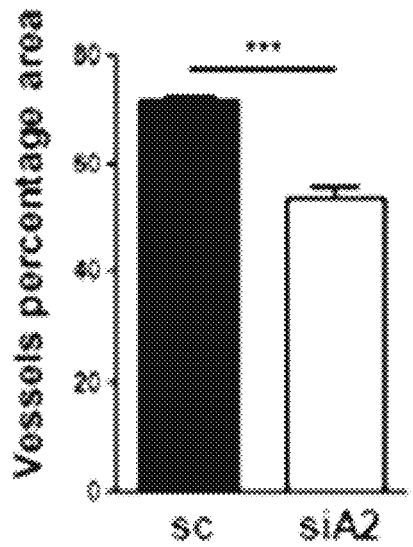

To define the function of AMIGO2 in vivo, AMIGO2-specific siRNA was subcutaneously injected, and expression of AMIGO2 was decreased (FIG. 2F to 2J), and significant decreases in hyaloid vessel structure was exhibited (FIGS. 2K and 2L). Further, retinal vessel growth and vascular areas were reduced (FIG. 2M to 2O). These data demonstrate that AMIGO2 regulates survival and growth of hyaloid and retinal vasculature in vivo.

AMIGO2 Controls Akt Activation In Vitro and In Vivo.

Figure 3A:
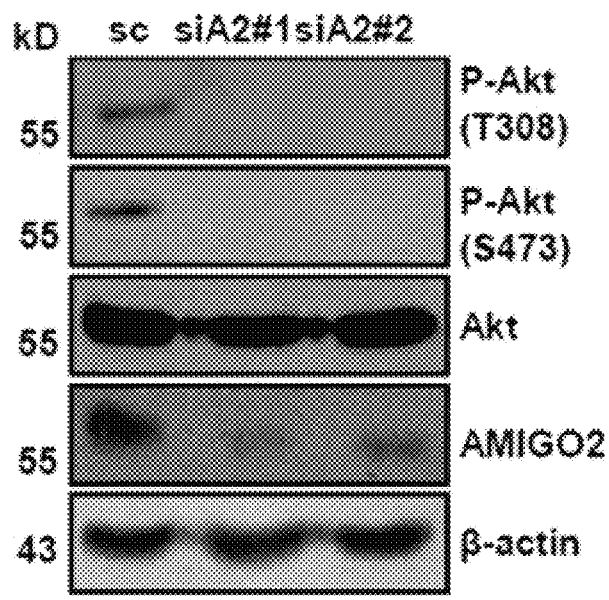
FIG. 3A shows the endogenous effect of AMIGO2 knockdown on Akt signaling in HUVECs. Two types of siA2 were evaluated.
Figure 3B:
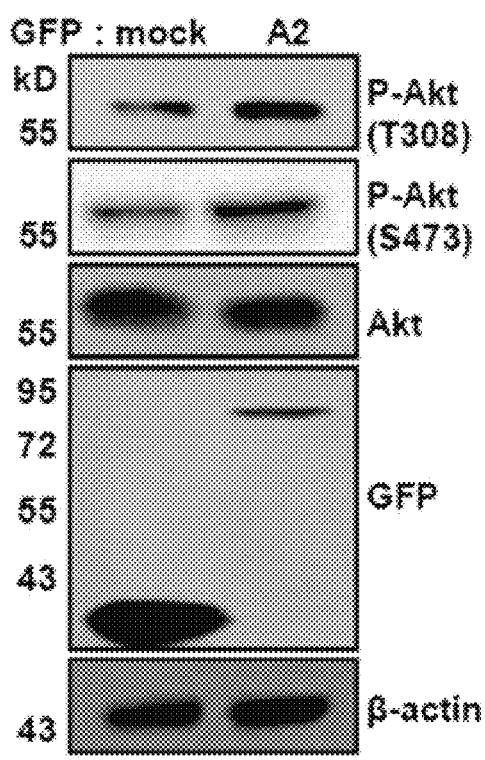
FIG. 3B shows endogenous effects of AMIGO2 overexpression on Akt signaling activation in HUVECs.

Akt phosphorylation (Thr308 and Ser473) was reduced in AMIGO2 siRNA-transfected HUVECs (FIG. 3A), whereas overexpression of AMIGO2 induced Akt activation in HUVEC (FIG. 3B).

To investigate whether VEGF-induced survival signaling was affected in AMIGO2-deficient ECs, AMIGO2-knockdown ECs were treated with VEGF at different time points (FIG. 2E). Interestingly, depletion of Amigo2 in mice using siRNA revealed decreased Akt phosphorylation in both hyaloid vessels and retinas (FIGS. 2I and 2J).

Figure 3C:
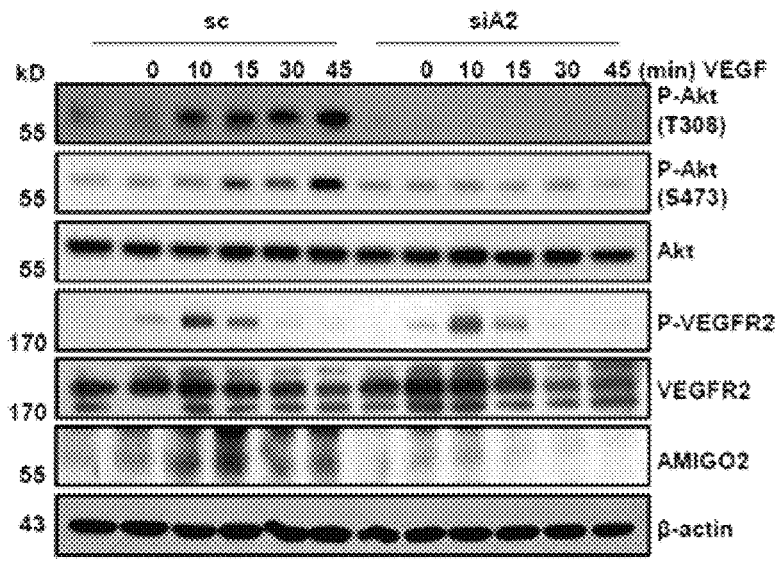
FIG. 3C shows temporal effects of AMIGO2 knockdown on VEGF (20 ng/mL)-induced signaling pathways in HUVECs.

To investigate the effects of VEGF, AMIGO2-knockdown ECs were treated with VEGF, and then activation of VEGF receptor 2 (VEGFR2) was unaffected, but Akt activation (Thr308 and Ser473) was inhibited in AMIGO2-knockdown ECs treated with VEGF (FIG. 3C).

Figure 3D:
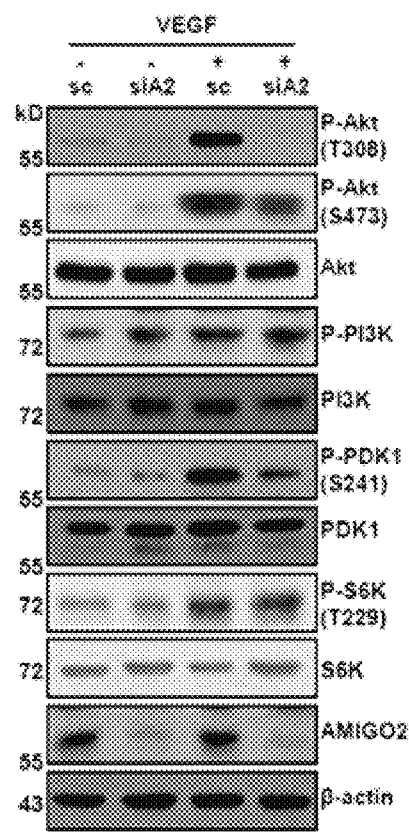
FIG. 3D shows VEGF-induced PI3K-PDK1-Akt signaling was evaluated in AMIGO2 siRNA-transfected HUVECs.

To narrow down the effect, we further examined the PI3K/Akt signaling pathway. Consequently, AMIGO2 knockdown in ECs did not affect the phosphorylation of PI3K, but phosphorylation of PDK1 was inhibited (FIG. 3D). These data suggest that AMIGO2 modulates EC survival and angiogenesis by regulating the PDK/Akt signaling pathway.

AMIGO2 Interacts with PDK1.

Figure 4A:
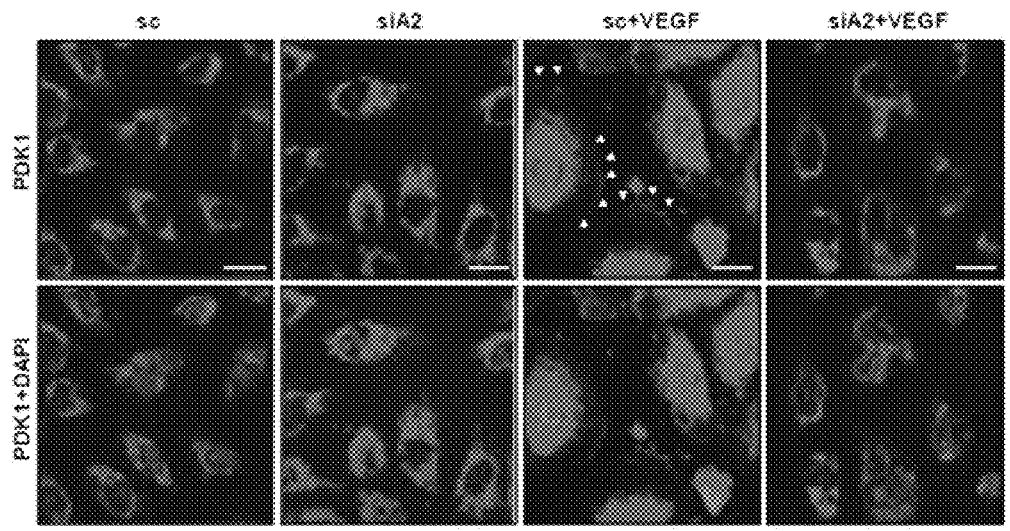
FIG. 4A shows PDK1 immunostaining that was performed in AMIGO2-inhibited HUVECs in the presence or absence of VEGF. Cells were starved for 4 hours and treated with VEGF. Scale bar: 25 µm.

To determine how AMIGO2 regulates the PDK1-mediated Akt pathway, we examined the cellular localization of PDK1 in AMIGO2-knockdown ECs. As a result, the membrane localization of PDK1 was not observed in AMIGO2-depleted ECs (FIG. 4A).

Figure 4B:
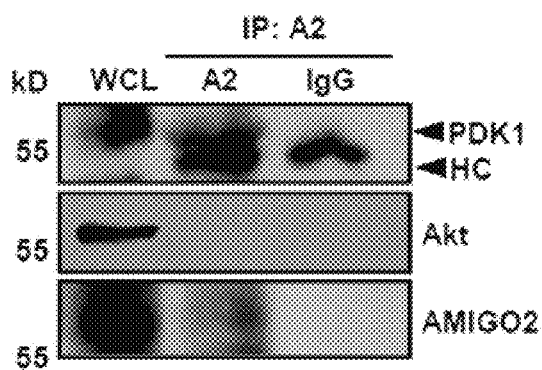
FIG. 4B shows endogenous AMIGO2 interacts with PDK1 in HUVECs. AMIGO2 was immunoprecipitated and blotted with anti-PDK1 and anti-Akt antibodies. Whole cell lysates=WCL, AMIGO2=A2, heavy chain=HC, normal IgG=IgG.
Figure 4C:
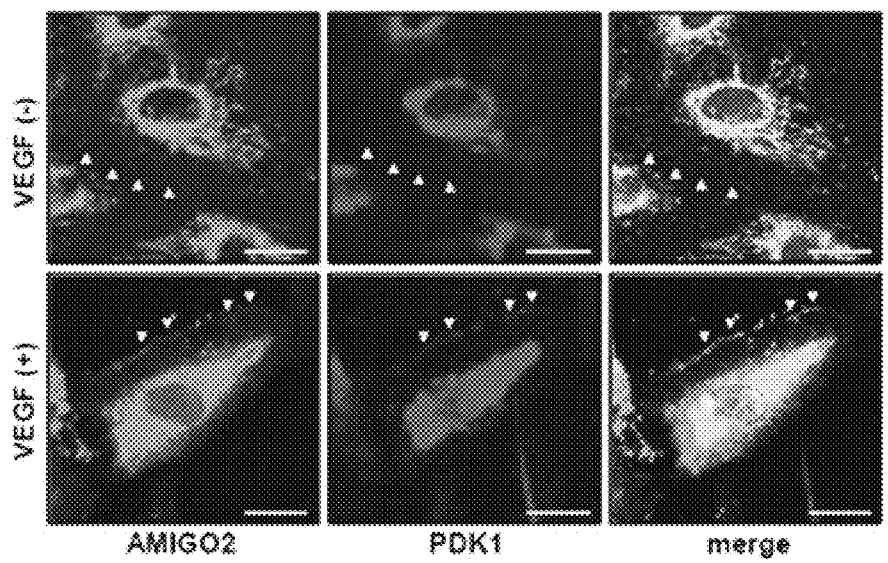
FIG. 4C shows co-localization of PDK1 and AMIGO2 in the plasma membrane and cytosol of HUVECs in the presence of VEGF. HUVECs were starved for 6 hours and stimulated with VEGF with or without. Scale bar: 20 µm.
Figure 4D:
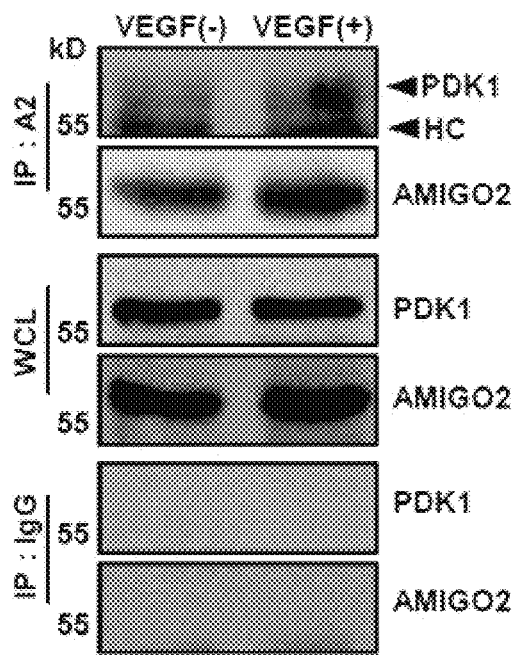
FIG. 4D shows that HUVECs were treated with VEGF and immunoprecipitated with an AMIGO2 antibody and blotted with endogenous PDK1.
Figure 4E:
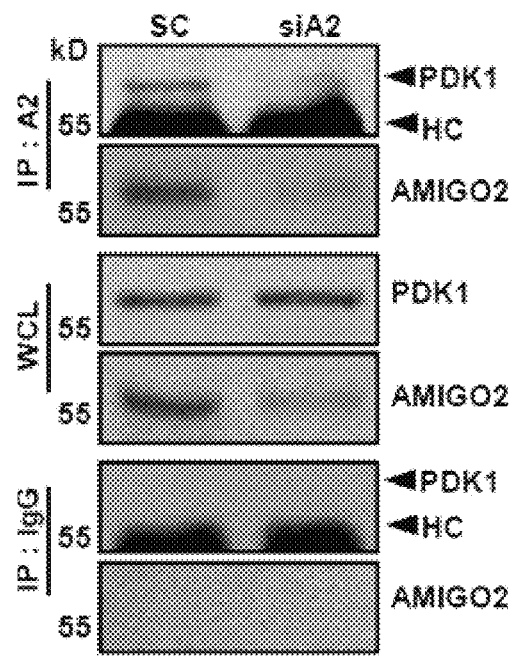
FIG. 4E shows that AMIGO2-deficient HUVECs were immunoprecipitated with an AMIGO2 antibody and blotted with an anti-PDK1 antibody.
Figure 4F:
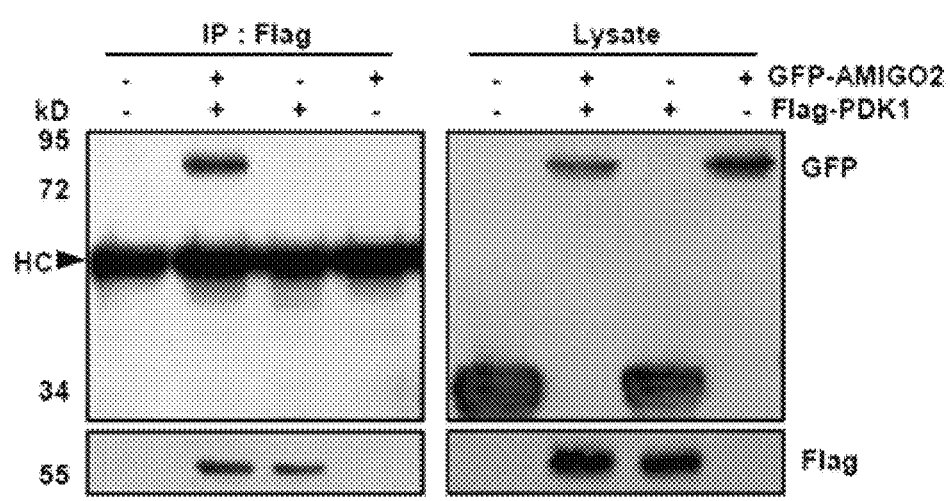
FIG. 4F shows that Flag-PDK1 was immunoprecipitated and blotted with an anti-GFP antibody tagged to AMIGO2.

Further, the interaction of AMIGO2 and PDK1 was revealed by immunoprecipitation assays (FIG. 4B), and co-localization was also revealed (FIG. 4C). With presence of VEGF, the association of AMOGO2 and PDK1 was increased (FIG. 4d), and PDK1 was almost undetectable in AMIGO2 immunoprecipitates from AMIGO2-knockdown ECs (FIG. 4E). Furthermore, co-immunoprecipitation assays revealed that GFP-AMIGO2 and Flag-PDK1 bind to each other (FIG. 4F). Taken together, these results indicate that AMIGO2 associates with PDK1 and regulates the localization of PDK1.

The AMIGO2 CD Interacts with the PDK1 PH Domain.

Figure 5A:
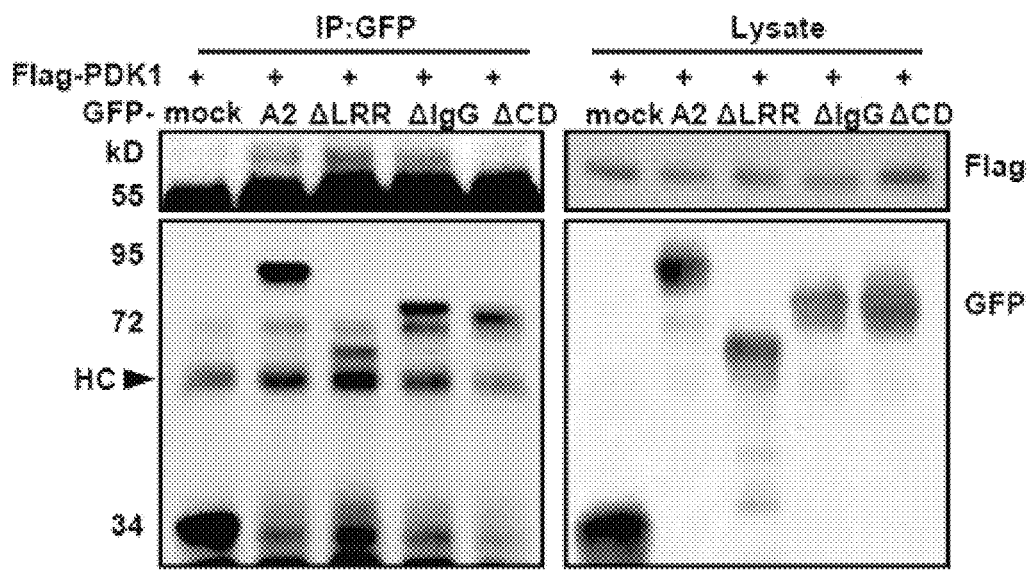
FIGS. 5A and 5B show the CD of AMIGO2 interacts with PDK1.GFP-tagged AMIGO2 and domain deletion mutants ($AMIGO2^{WT}$=A2; $AMIGO2^{\Delta LRR}$=ΔLRR; $AMIGO2^{\Delta IgG}$=ΔIgG; $AMIGO2^{\Delta CD}$=ΔCD; or CD=CD domain of AMIGO2) were immunoprecipitated and blotted with the Flag antibody. PDK1 was immunoprecipitated with the Flag antibody and detected with the anti-GFP antibody.
Figure 5B:
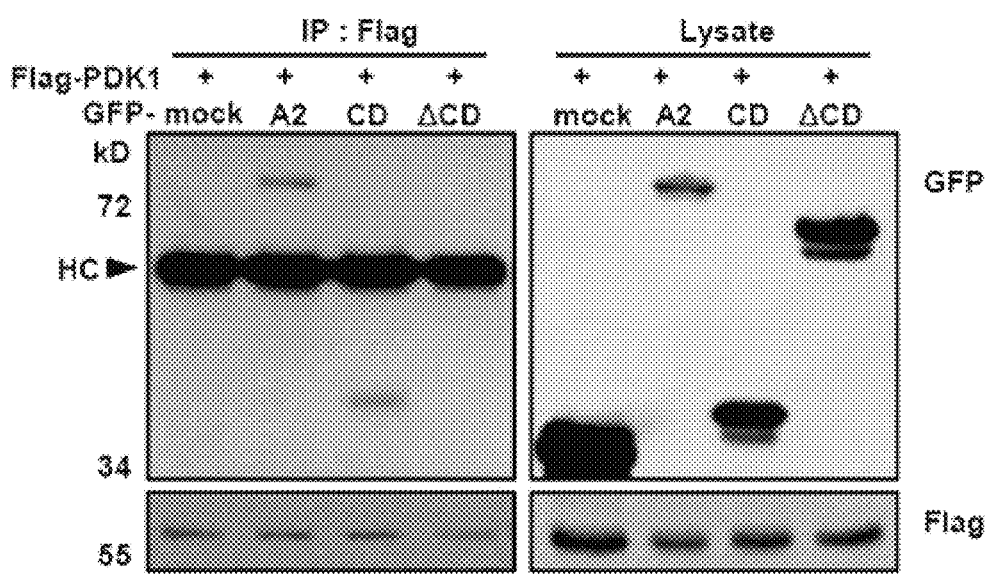
Figure 5C:
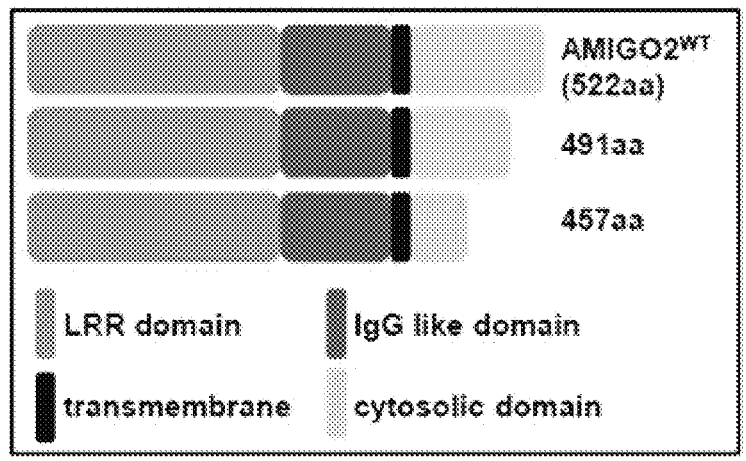
FIG. 5C shows schematic diagram of 491aa and 457aa of the AMIGO2 constructs.

The binding domain of AMIGO2 and PDK1 that were responsible for the interaction was explored. Plasmids containing AMIGO2 without each domain were immunoprecipitated with Flag-PDK1, and it was revealed that AMIGO2 without cytosolic Domain did not associate with PDK1 (FIG. 5A). To verify the interaction of the CD and PDK1, the protein that only contains the CD domain was immunoprecipitated with Flag-PCK1, and the association of the two above proteins (FIGS. 5B and 5C).

Figure 5D:
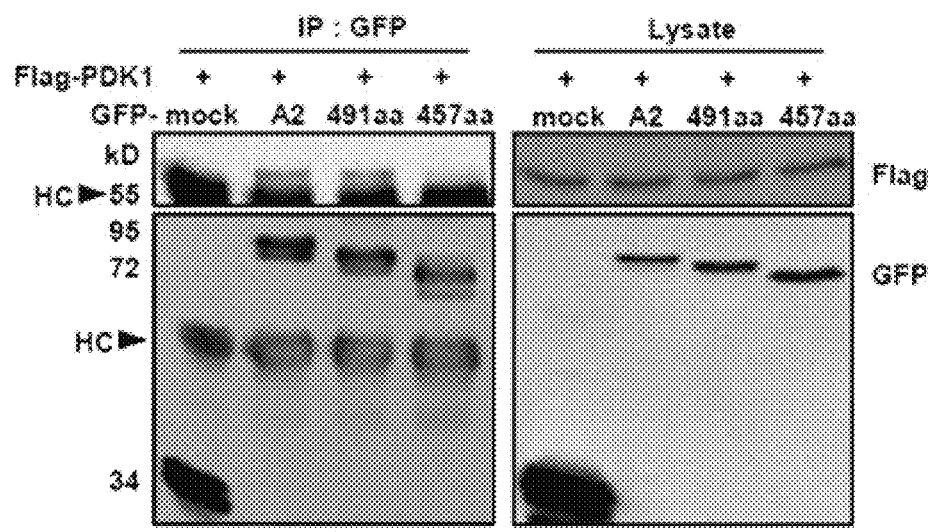
FIG. 5D shows PDK1 associates with the region between 491aa and 457aa of AMIGO2. GFP-tagged AMIGO2 and domain deletion mutants were immunoprecipitated and blotted with the Flag antibody.

To elucidate the segment of the CD of AMIGO2 that interacts with PDK1, co-immunoprecipitation was conducted with variously truncated CD domains. As a result, the AMIGO2$^{491}$aa was co-immunoprecipitated with Flag-PDK1, but not AMIGO2$^{457}$aa (FIG. 5D). Analysis of the AMIGO family CD revealed highly conserved sequences between 457aa and 491aa (FIG. 5E).

To clarify the domain of PDK1 that interacts with the CD of AMIGO2, pull-down assay was conducted with the purified PH domain or the purified kinase domain. The assay showed the interaction between PH domain of PDK1 and CD of AMIGO2 (FIG. 5F).

Figure 5G:
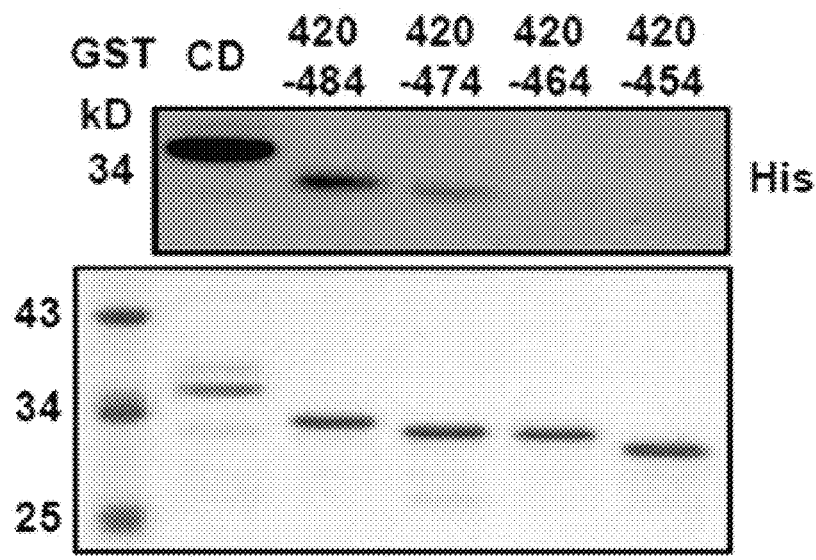
FIG. 5G shows Far-western analysis that was performed for each truncated mutant. Coomassie Blue staining revealed purified GST-tagged truncated mutants that were previously loaded for Far-western analysis.
Figure 5H:
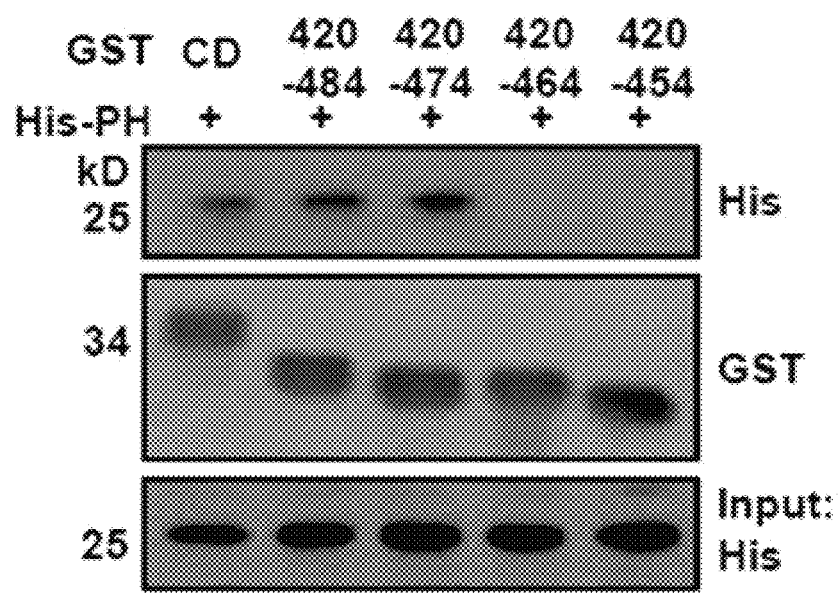
FIG. 5H shows the western blot result. The mixtures of purified GST-tagged truncated mutants and His-tagged PH domain proteins were pulled down with GST beads, eluted, and the western blot was performed using His and GST antibodies.

To clarify the regions that directly interact with the PH domain of PDK1, pull-down assay of variously truncated CD mutants was conducted with PH domain of PDK1. The purified GST-tagged AMIGO2$^{CD}$, 420-484, and 420-474 directly interacted with purified His-PDK1$^{PH}$, but not GST-tagged 420-464 and 420-454 (FIGS. 5g and 5h). Interestingly, the peptide sequences between 465 and 474 are RVVFLEPLKD (SEQ ID NO: 39), which is highly conserved among the AMIGO family.

Thus, the peptide sequence RVVFLEPLKD (SEQ ID NO: 39) of AMIGO2 directly binds to the PH domain of PDK1 to control the PDK1/Akt signaling pathways.

Protein Transduction Domain (PTD)-A2, a Peptide from the CD of AMIGO2, Controls Akt Activation, and Angiogenesis.

Figure 6A:
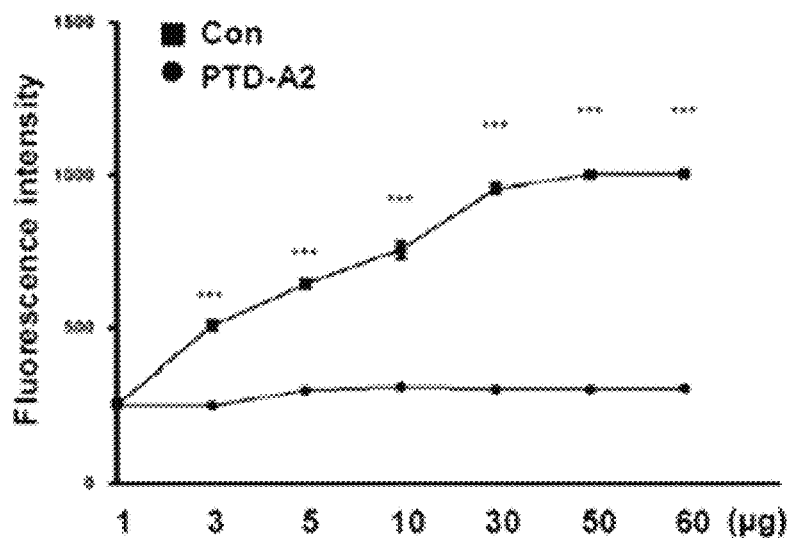
FIG. 6A shows the PTD-A2 binding assay result. PH domain proteins (0-60 µg) were incubated with FITC-PTD-A2 and detected by fluorescence.
Figure 6B:
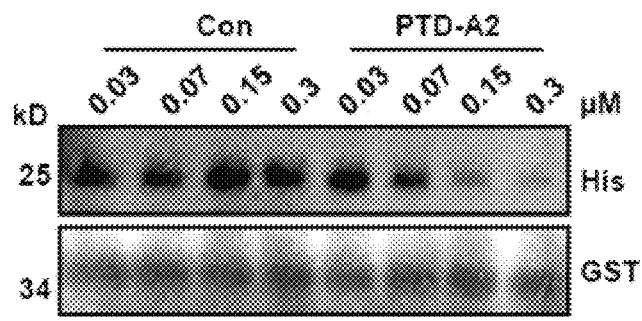
FIG. 6B shows peptide competition assay with Con or PTD-A2 and CD to PH domains. His-tagged PDK1PH was incubated with purified $GST-AMIGO2^{CD}$ and Con or PTD-A2 in a dose dependent manner.

To evaluate whether the AMIGO2 CD regulates endothelial cell viability, HUVECs were transfected with AMIGO2CD, treated with VEGF, and cell apoptosis was examined. AMIGO2 CD-transfected ECs revealed higher apoptotic rates. Thus, the peptide sequence RVVFLEPLKD (SEQ ID NO: 39) was conjugated with FITC and cell penetrating peptide (PTD-A2). PTD-A2 bound to the PDK1 PH domain and inhibited the interaction of the CD of AMIGO2 and PH domain of PDK1 (FIG. 6a and FIG. 6b).

Figure 6C:
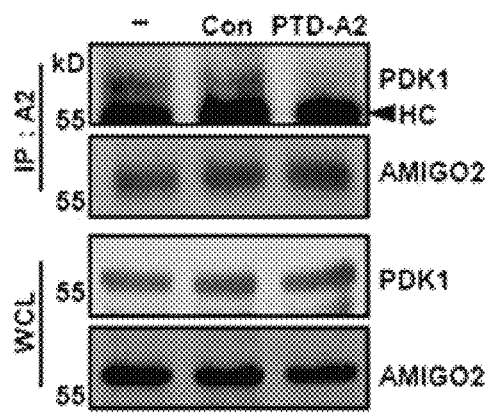
FIG. 6C shows that Con and PTD-A2 treated HUVECs were immunoprecipitated with an AMIGO2 antibody and blotted with anti-PDK1 and AMIGO2 antibodies. Hc=HUVEC as a control sample.
Figure 6D:
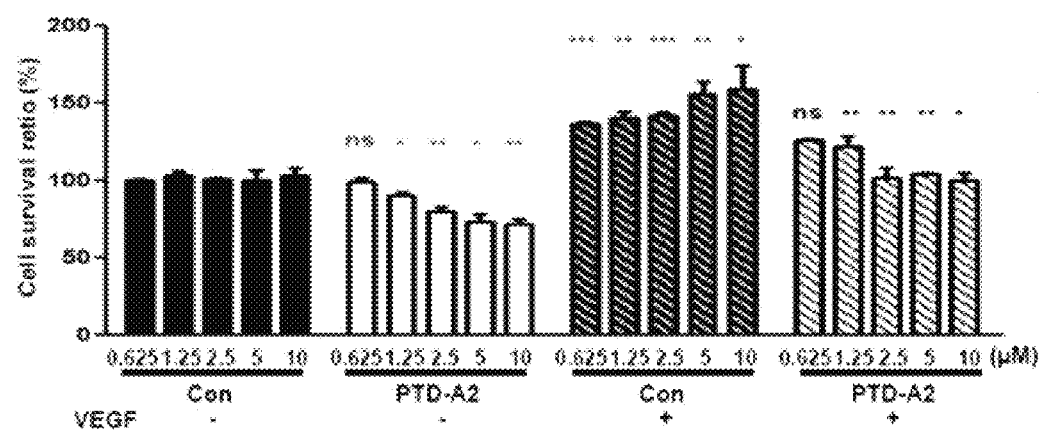
FIGS. 6D and 6E show cell viability of PTD-A2-treated HUVECs under conditions of serum-free starvation with or without VEGF in a dose- and time-dependent manner (n=6; * p<0.05;  p<0.005; * p<0.0001).
Figure 6E:
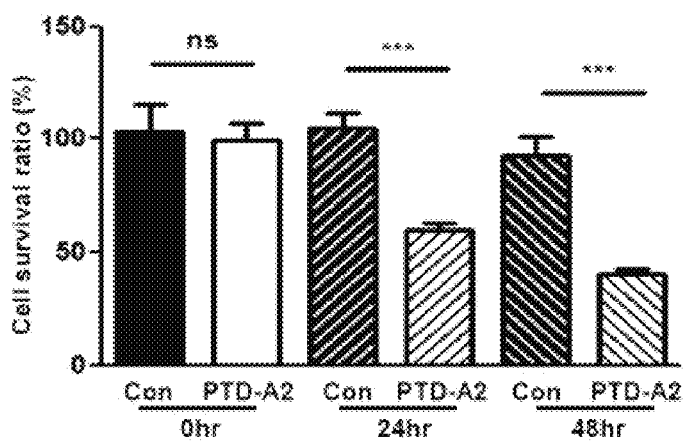

In Endothelial cells treated with PTD-A2, the association between AMIGO2 and PDK1 was inhibited (FIG. 6c). PTD-A2-treated HUVECs exhibited a dose and time-dependent inhibitory effect on cell viability (FIGS. 6d and 6e).

Figure 6F:
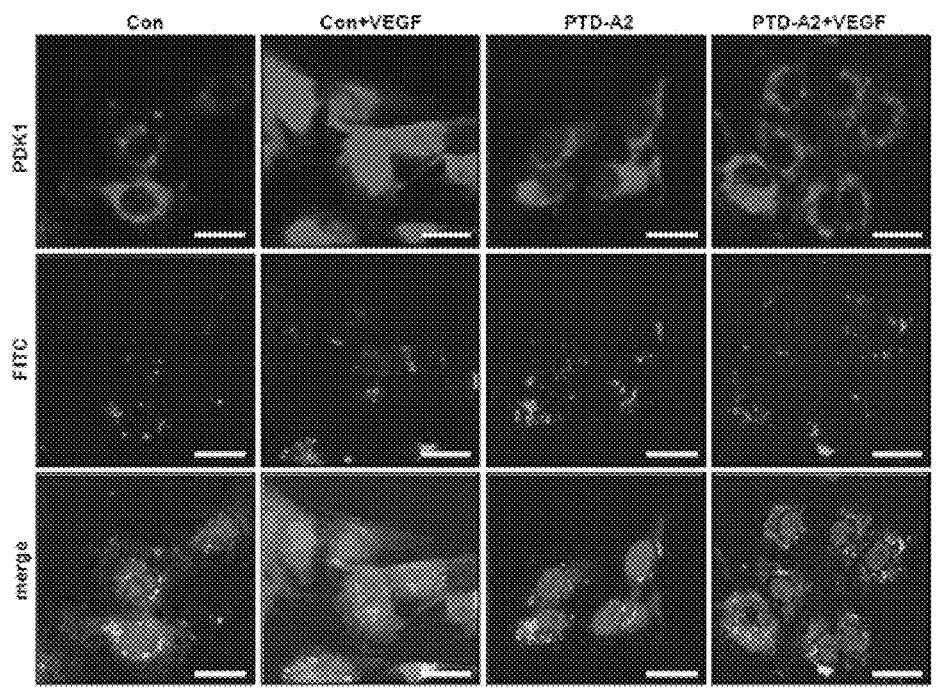
FIG. 6F shows localization of PDK1 in the plasma membrane and cytosol of HUVECs in the presence of VEGF after Con or PTD-A2 treatment. Scale bar: 20 μm.
Figure 6G:
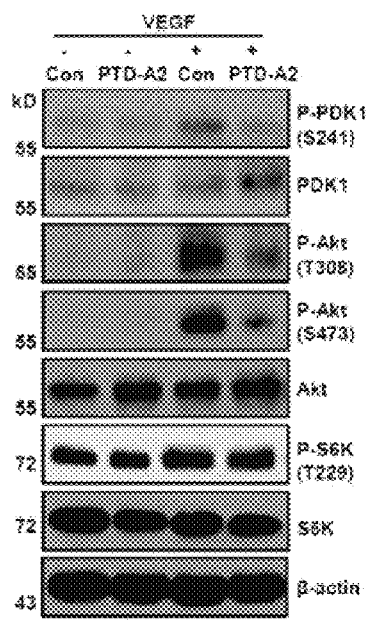
FIG. 6G shows effects of PTD-A2 on VEGF-induced Akt signaling in HUVECs.
Figure 6H:
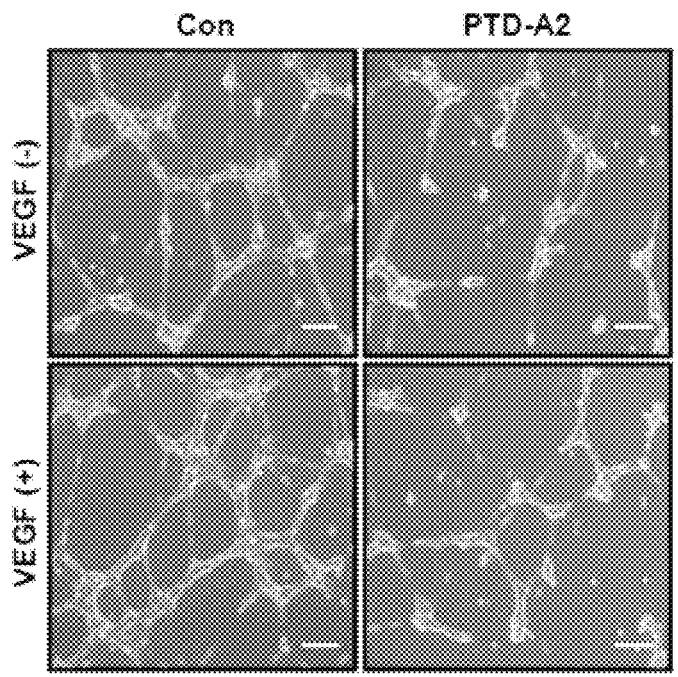
FIGS. 6H and 6I show PTD-A2 Matrigel™-induced tube formation that was assessed in HUVECs. Scale bar: 200 μm. Tube lengths are presented as the percent of total tube length per field versus control cells (n=5;  $p<0.005$; *$p<0.0005$).
Figure 6I:
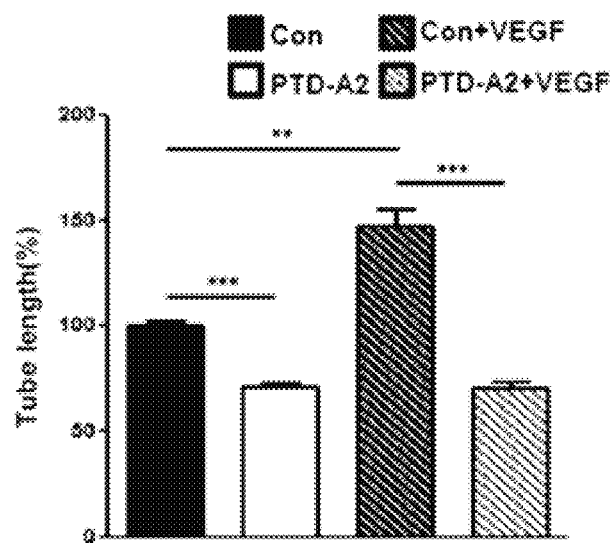
Figure 6J:
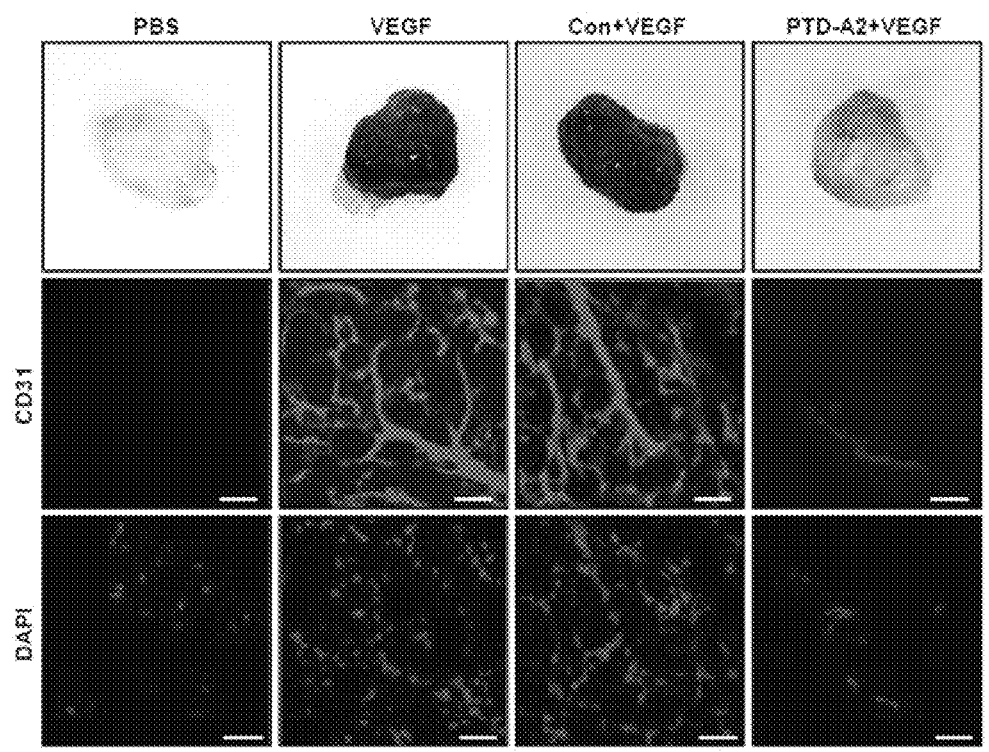
FIG. 6J shows Male C57BL/6 mice (n=6 per group) received subcutaneous injections of Matrigel™ containing PBS, VEGF (200 ng), Con (25 μM) with VEGF, or PTD-A2 (25 μM) with VEGF. Matrigel™ plugs were removed five days after implantation, fixed, sectioned, and stained for immunohistochemistry with anti-CD31 antibody (red) for the identification of endothelial vessels. DAPI (blue) was used for nuclei labeling and visualization was performed using confocal microscopy. Scale bar: 50 μm.
Figure 6K:
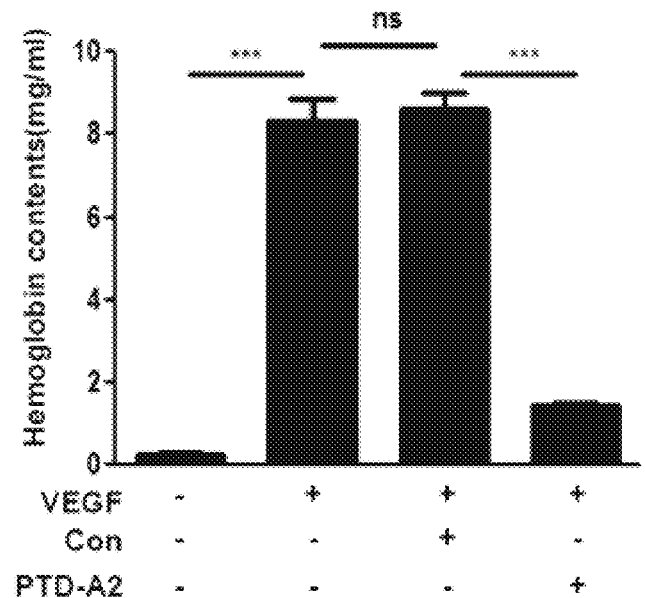
FIG. 6K shows quantification of neovessel formation by measuring hemoglobin in the Matrigel™.
Figure 6L:
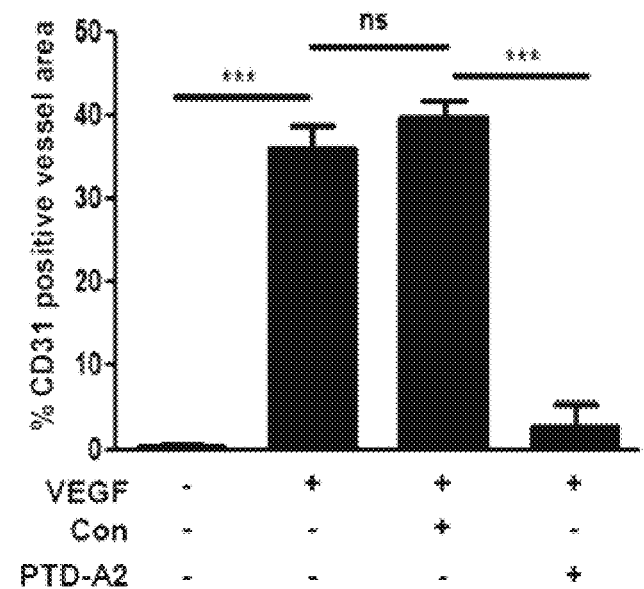
FIG. 6L shows quantitative assessment of CD31 positive ECs. *** $p<0.0005$; ns: not significant. Data are means±SD.
Figure 6M:
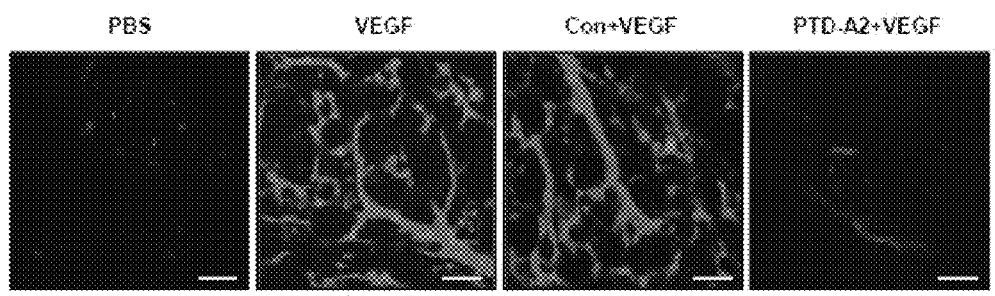
FIG. 6M shows Merged images of Matrigel™ containing PBS, VEGF (200 ng), Con (25 μM) with VEGF, or PTDA2 (25 μM) with VEGF. Immunolabeling with anti-CD31 antibody (red) and DAPI (blue) were used. Scale bar: 50 μm.

To test the hypothesis that PTD-A2 potentially blocks PDK1 localization to the plasma membrane, the alteration of PDK1 localization following VEGF treatment was verified. As a result, PDK1 was unable to move to the plasma membrane in PTD-A2-treated HUVECs (FIG. 6F). As well, PTD-A2-treated HUVECs reduced the activity of both Akt and PDK1 (FIG. 6G). Matrigel-induced tube formation in PTD-A2 treated ECs was inhibited (FIGS. 6H and 6I), and Matrigel plug assay showed the dramatic inhibition of neovascularization in Matrigel plugs containing PTD-A2 with VEGF, which was confirmed by lower hemoglobin contents and histological staining with CD31 (FIGS. 6J to 6M).

Taken together, the results indicate that PTD-A2 affects cell viability and angiogenesis by blocking the localization and activation of PDK1.

PTD-A2 Reveals an Anti-Angiogenic Activity in Pathological Angiogenesis and Tumor Growth.

The model of oxygen-induced retinopathy (OIR) has been used extensively in retinopathy of prematurity, proliferative diabetic retinopathy, and for evaluating the efficacy of anti-angiogenic molecules. Therefore, the inventors conduct the experiments using the OIR model groups treated with PBS, Con-pep or PTD-A2. As a result, the retinas of mice injected with PTD-A2 exhibited increased avascular areas and significantly reduced retinal hemorrhage, vascular areas, and tuft formation (FIGS. 6I to 6L).

To examine the antitumor angiogenic activity of PTD-A2, tumors were generated by injection of B16F10 melanoma tumors to mice followed by each treatment with PBS, Con-pep or PTD-A2. Interestingly, the tumor formation and angiogenesis were decreased in the PTD-A2 injected mice (FIG. 7A to 7E).

Figure 7A:
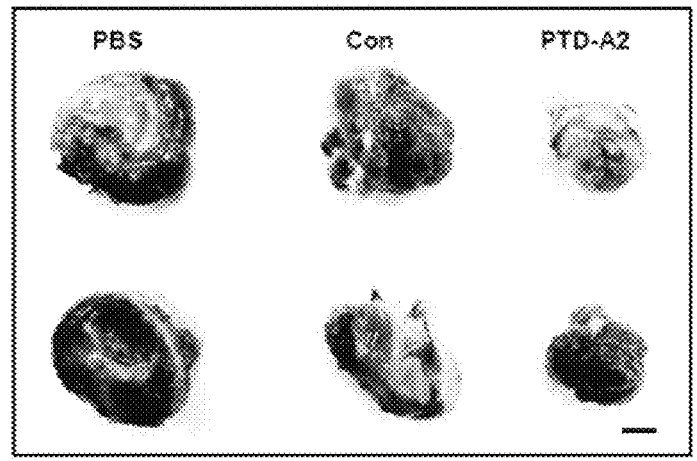
FIGS. 7A to 7G show that treatment with PTD-A2 inhibits tumor growth, neovessel formation, and tumor cell viability in B16F10 tumors.
Figure 7B:
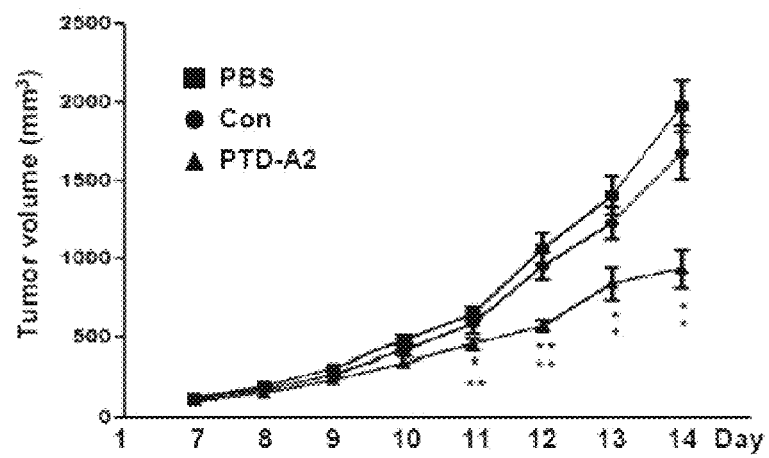
Figure 7C:
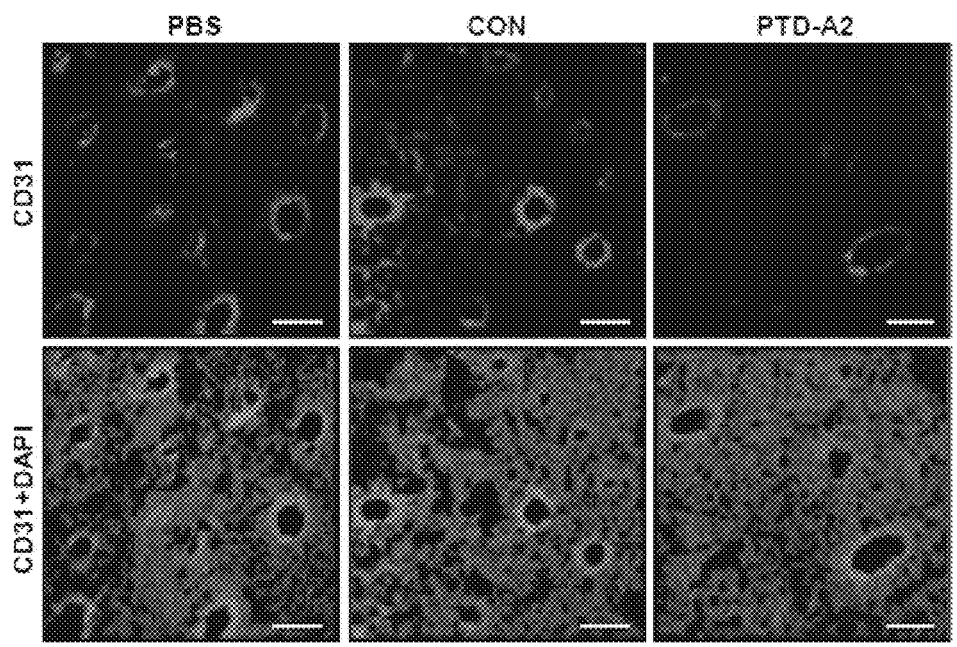
Figure 7D:
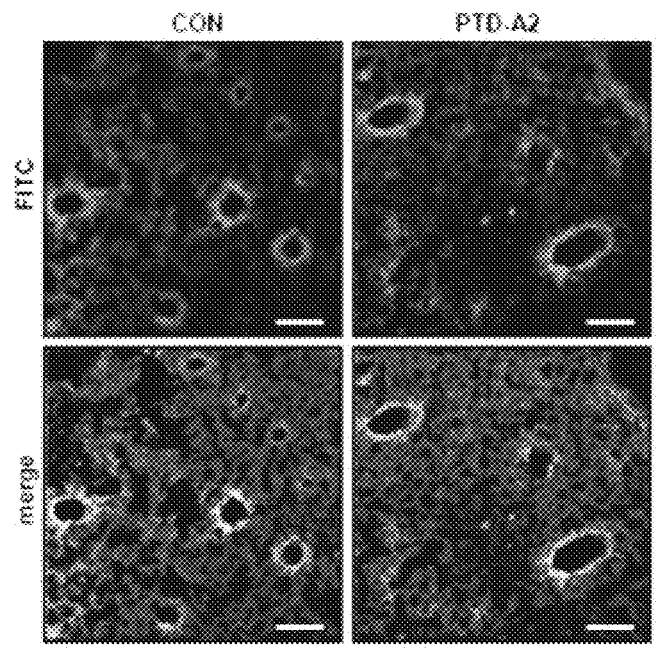
Figure 7E:
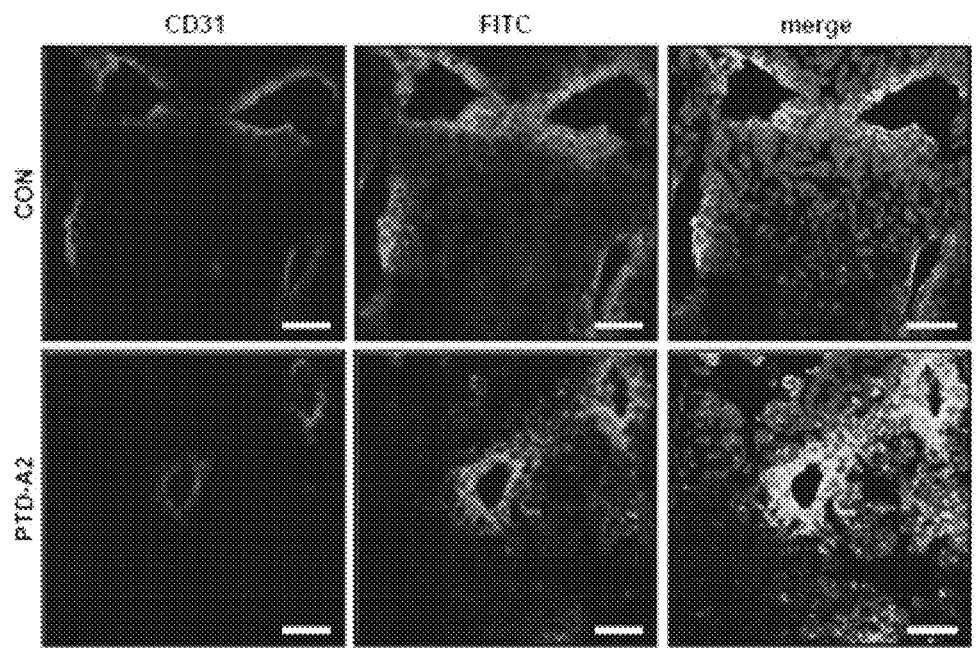
Figure 7F:
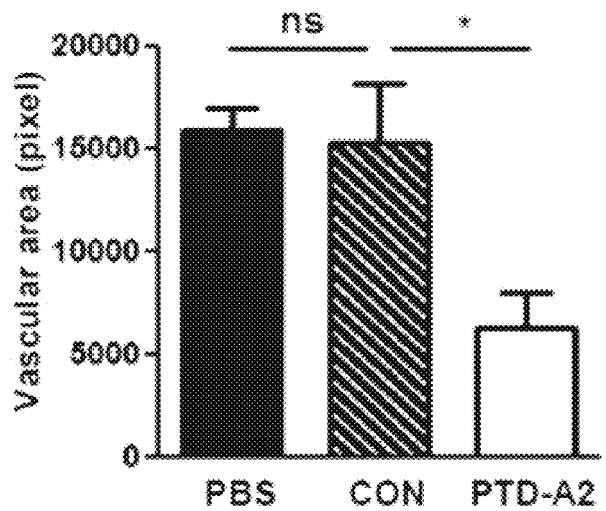
Figure 7G:
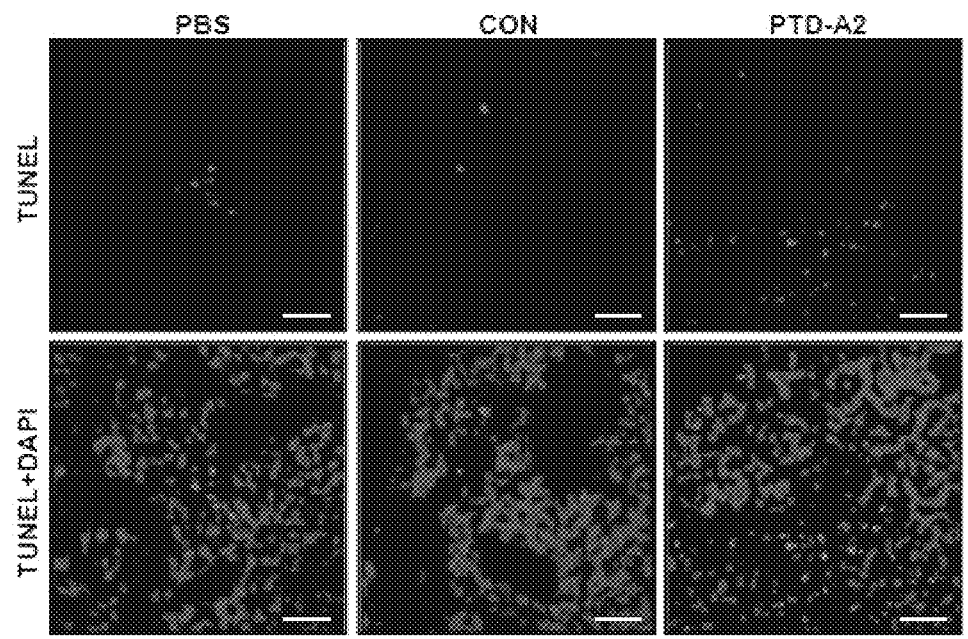

Compared to the PBS or Con-pep injected groups, the increased apoptotic regions of tumors of PTD-A2 injected mice were confirmed by TUNEL assay (FIGS. 7F and 7G).

These results demonstrate that treatment with PTD-A2 might be essential for blocking tumor growth and pathological angiogenesis.

REFERENCES

Alvarez, Y., O. Astudillo, L. Jensen, A. L. Reynolds, N. Waghorne, D. P. Brazil, Y. Cao, J. J. O'Connor, and B. N. Kennedy. 2009. Selective inhibition of retinal angiogenesis by targeting PI3 kinase. PLoS ONE. 4.

Bayascas, J. R., S. Wullschleger, K. Sakamoto, J. M. Garcia-Martinez, C. Clacher, D. Komander, D. M. F. Van Aalten, K. M. Boini, F. Lang, C. Lipina, L. Logie, C. Sutherland, J. A. Chudek, J. A. Van Diepen, P. J. Voshol, J. M. Lucocq, and D. R. Alessi. 2008. Mutation of the PDK1 PH domain inhibits protein kinase B/Akt, leading to small size and insulin resistance. Molecular and Cellular Biology. 28:3258-3272.

Behlke, M. A. 2006. Progress towards in vivo use of siRNAs. Molecular Therapy. 13:644-670.

Bischoff, J. 1995. Approaches to studying cell adhesion molecules in angiogenesis. Trends in Cell Biology. 5:69-74.

Bonifazi, P., C. D'Angelo, S. Zagarella, T. Zelante, S. Bozza, A. De Luca, G. Giovannini, S. Moretti, R. G. Iannitti, F. Fallarino, A. Carvalho, C. Cunha, F. Bistoni, and L. Romani. 2010. Intranasally delivered siRNA targeting PI3K/Akt/mTOR inflammatory pathways protects from aspergillosis. Mucosal Immunology. 3:193-205.

Casamayor, A., N. A. Morrice, and D. R. Alessi. 1999. Phosphorylation of Ser-241 is essential for the activity of 3-phosphoinositide-dependent protein kinase-1: Identification of five sites of phosphorylation in vivo. Biochemical Journal. 342:287-292.

Chang, L., P. H. Graham, J. Hao, J. Ni, J. Bucci, P. J. Cozzi, J. H. Kearsley, and Y. Li. 2013. Acquisition of epithelial mesenchymal transition and cancer stem cell phenotypes is associated with activation of the PI3K/Akt/mTOR pathway in prostate cancer radioresistance. Cell Death and Disease. 4.

Chang, Z., Q. Zhang, Q. Feng, J. Xu, T. Teng, Q. Luan, C. Shan, Y. Hu, B. A. Hemmings, X. Gao, and Z. Yang. 2010. Deletion of Akt1 causes heart defects and abnormal cardiomyocyte proliferation. Developmental Biology. 347:384-391.

Chen, X., Y. Zhang, Y. Wang, D. Li, L. Zhang, K. Wang, X. Luo, Z. Yang, Y. Wu, and J. PDK1 regulates platelet activation and arterial thrombosis. Blood. 121:3718-3726.

Chen, Y., S. Aulia, L. Li, and B. L. Tang. 2006. AMIGO and friends: An emerging family of brain enriched, neuronal growth modulating, type I transmembrane proteins with leucine-rich repeats (LRR) and cell adhesion molecule motifs. Brain Research Reviews. 51:265-274.

Choi, Y. S., H. J. Choi, J. K. Min, B. J. Pyun, Y. S. Maeng, H. Park, J. Kim, Y. M. Kim, and Y. G. Kwon. 2009. Interleukin-33 induces angiogenesis and vascular permeability through ST2/TRAF6-mediated endothelial nitric oxide production. Blood. 114:3117-3126.

Connor, K. M., N. M. Krah, R. J. Dennison, C. M. Aderman, J. Chen, K. I. Guerin, P. Sapieha, A. Stahl, K. L. Willett, and L. E. H. Smith. 2009. Quantification of oxygen-induced retinopathy in the mouse: A model of vessel loss, vessel regrowth and pathological angiogenesis. Nature Protocols. 4:1565-1573. Datta, S. R., A. Brunet, and M. E. Greenberg. 1999. Cellular survival: A play in three akts. Genes and Development. 13:2905-2927.

Dimmeler, S., and A. M. Zeiher. 2000a. Akt takes center stage in angiogenesis signaling. Circulation Research. 86:4-5.

Dimmeler, S., and A. M. Zeiher. 2000b. Endothelial cell apoptosis in angiogenesis and vessel regression. Circulation Research. 87:434-439.

Feng, Q., R. Di, F. Tao, Z. Chang, S. Lu, W. Fan, C. Shan, X. Li, and Z. Yang. 2010. PDK1 regulates vascular remodeling and promotes epithelial-mesenchymal transition in cardiac development.

Molecular and Cellular Biology. 30:3711-3721.

Fujio, Y., and K. Walsh. 1999. Akt mediates cytoprotection of endothelial cells by vascular endothelial growth factor in an anchorage-dependent manner. Journal of Biological Chemistry. 274:16349-16354.

Gao, X., and T. K. Harris. 2006. Role of the PH domain in regulating in vitro autophosphorylation events required for reconstitution of PDK1 catalytic activity. Bioorganic Chemistry. 34:200-223.

Garuti, L., M. Roberti, and G. Bottegoni. 2010. Non-ATP competitive protein kinase inhibitors. Liu. 2013. Current Medicinal Chemistry. 17:2804-2821.

Goenaga, D., C. Hampe, N. Carre K. Cailliau, E. Browaeys-Poly, D. Perdereau, L. J. Holt, R. J. Daly, C. Girard, I. Broutin, T. Issad, and A. F. Burnol. 2009. Molecular determinants of Grb14-mediated inhibition of insulin signaling. Molecular Endocrinology. 23:1043-1051.

Hirai, H., H. Sootome, Y. Nakatsuru, K. Miyama, S. Taguchi, K. Tsujioka, Y. Ueno, H. Hatch, P. K. Majumder, B. S. Pan, and H. Kotani. 2010. MK-2206, an allosteric akt inhibitor, enhances antitumor efficacy by standard chemotherapeutic agents or molecular targeted drugs in vitro and in vivo. Molecular Cancer Therapeutics. 9:1956-1967.

Huang, B. X., M. Akbar, K. Kevala, and H. Y. Kim. 2011. Phosphatidylserine is a critical modulator for Akt activation. Journal of Cell Biology. 192:979-992.

Inaba, S., S. Nagahara, N. Makita, Y. Tarumi, T. Ishimoto, S. Matsuo, K. Kadomatsu, and Y. Takei. 2012. Atelocollagen-mediated systemic delivery prevents immunostimulatory adverse effects of siRNA in mammals. Molecular Therapy. 20:356-366.

Jiang, B. H., and L. Z. Liu. 2008. PI3K/PTEN signaling in tumorigenesis and angiogenesis. Biochimica et Biophysica Acta—Proteins and Proteomics. 1784:150-158.

Jing, F. S., T. Phung, I. Shiojima, T. Felske, J. N. Upalakalin, D. Feng, T. Kornaga, T. Dor, A. M. Dvorak, K. Walsh, and L. E. Benjamin. 2005. Microvascular patterning is controlled by fine tuning the Akt signal. Proceedings of the National Academy of Sciences of the United States of America. 102:128-133.

King, C. C., and A. C. Newton. 2004. The adaptor protein Grb14 regulates the localization of 3-phosphoinositide-dependent kinase-1. Journal of Biological Chemistry. 279:37518-37527.

King, W. G., M. D. Mattaliano, T. O. Chan, P. N. Tsichlis, and J. S. Brugge. 1997. Phosphatidylinositol 3-kinase is required for integrin-stimulated AKT and Raf-1/mitogen-activated protein kinase pathway activation. Molecular and Cellular Biology. 17:4406-4418.

Kuja-Panula, J., M. Kiiltomaki, T. Yamashiro, A. Rouhiainen, and H. Rauvala. 2003. AMIGO, a transmembrane protein implicated in axon tract development, defines a novel protein family with leucine-rich repeats. Journal of Cell Biology. 160:963-973.

Lamalice, L., F. Le Boeuf, and J. Huot. 2007. Endothelial cell migration during angiogenesis. Circulation Research. 100:782-794.

Lim, M. A., C. K. Kikani, M. J. Wick, and L. Q. Dong. 2003. Nuclear translocation of 3'-phosphoinositide-dependent protein kinase 1 (PDK-1): A potential regulatory mechanism for PDK-1 function. Proceedings of the National Academy of Sciences of the United States of America. 100:14006-14011.

Liu, W., S. A. Ahmad, N. Reinmuth, R. M. Shaheen, Y. D. Jung, F. Fan, and L. M. Ellis. 2000. Endothelial cell survival and apoptosis in the tumor vasculature. Apoptosis. 5:323-328.

Lobov, I. B., S. Rao, T. J. Carroll, J. E. Vallance, M. Ito, J. K. Ondr, S. Kurup, D. A. Glass, M. S. Patel, W. Shu, E. E. Morrisey, A. P. McMahon, G. Karsenty, and R. A. Lang. 2005. WNT7b mediates macrophage-induced programmed cell death in patterning of the vasculature. Nature. 437:417-421.

Maeng, Y. S., H. J. Choi, J. Y. Kwon, Y. W. Park, K. S. Choi, J. K. Min, Y. H. Kim, P. G. Suh, K. S. Kang, M. H. Won, Y. M. Kim, and Y. G. Kwon. 2009. Endothelial progenitor cell homing: Prominent role of the IGF2-IGF2R-PLC 22 axis. Blood. 113:233-243.

Mammoto, A., K. M. Connor, T. Mammoto, C. W. Yung, D. Huh, C. M. Aderman, G. Mostoslaysky, L. E. H. Smith, and D. E. Ingber. 2009. A mechanosensitive transcriptional mechanism that controls angiogenesis. Nature. 457:1103-1108.

Marin, V., G. Kaplanski, S. Gres, C. Farnarier, and P. Bongrand. 2001. Endothelial cell culture: Protocol to obtain and cultivate human umbilical endothelial cells. Journal of Immunological Methods. 254:183-190.

Maroulakou, I. G., W. Oemler, S. P. Naber, and P. N. Tsichlis. 2007. Akt1 ablation inhibits, whereas Akt2 ablation accelerates, the development of mammary adenocarcinomas in mouse mammary tumor virus (MMTV)-ErbB2/Neu and MMTV-polyoma middle T transgenic mice. Cancer Research. 67:167-177.

Martelli, A. M., P. L. Tazzari, G. Tabellini, R. Bortul, A. M. Billi, L. Manzoli, A. Ruggeri, R. Conte, and L. Cocco. 2003. A new selective AKT pharmacological inhibitor reduces resistance to chemotherapeutic drugs, TRAIL, all-trans-retinoic acid, and ionizing radiation of human leukemia cells. Leukemia. 17:1794-1805.

Meuillet, E. J., S. Zuohe, R. Lemos, N. Ihle, J. Kingston, R. Watkins, S. A. Moses, S. Zhang, L. Du-Cuny, R. Herbst, J. J. Jacoby, L. L. Zhou, A. M. Ahad, E. A. Mash, D. L. Kirkpatrick, and G. Powis. 2010. Molecular pharmacology and antitumor activity of PHT-427, a novel akt/phosphatidylinositide-dependent protein kinase 1 pleckstrin homology domain inhibitor. Molecular Cancer Therapeutics. 9:706-717.

Mora, A., D. Komander, D. M. F. Van Aalten, and D. R. Alessi. 2004. PDK1, the master regulator of AGC kinase signal transduction. Seminars in Cell and Developmental Biology. 15:161-170.

Nakamura, A., M. Naito, T. Tsuruo, and N. Fujita. 2008. Freud-1/Aki1, a novel PDK1-interacting protein, functions as a scaffold to activate the PDK1/Akt pathway in epidermal growth factor signaling. Molecular and Cellular Biology. 28:5996-6009.

Nakamura, T., T. Kuwai, Y. Kitadai, T. Sasaki, D. Fan, K. R. Coombes, S. J. Kim, and I. J. Fidler. 2007. Zonal heterogeneity for gene expression in human pancreatic carcinoma. Cancer Research. 67:7597-7604.

Ono, T., N. Sekino-Suzuki, Y. Kikkawa, H. Yonekawa, and S. Kawashima. 2003. Alivin 1, a novel neuronal activity-dependent gene, inhibits apoptosis and promotes survival of cerebellar granule neurons. Journal of Neuroscience. 23:5887-5896.

Pearce, L. R., D. Komander, and D. R. Alessi. 2010. The nuts and bolts of AGC protein kinases. Nature Reviews Molecular Cell Biology. 11:9-22.

Pearn, L., J. Fisher, A. K. Burnett, and R. L. Darley. 2007. The role of PKC and PDK1 in monocyte lineage specification by Ras. Blood. 109:4461-4469.

Portt, L., G. Norman, C. Clapp, M. Greenwood, and M. T. Greenwood. 2011. Anti-apoptosis and cell survival: A review. Biochimica et Biophysica Acta (BBA)—Molecular Cell Research. 1813:238-259.

Primo, L., L. Di Blasio, C. Roca, S. Droetto, R. Piva, B. Schaffhausen, and F. Bussolino. 2007. Essential role of PDK1 in regulating endothelial cell migration. Journal of Cell Biology. 176:1035-1047.

Pullen, N., P. B. Dennis, M. Andjelkovic, A. Dufner, S. C. Kozma, B. A. Hemmings, and G. Thomas. 1998. Phosphorylation and activation of p70 (s6k) by PDK1. Science. 279:707-710.

Rabenau, K. E., J. M. O'Toole, R. Bassi, H. Kotanides, L. Witte, D. L. Ludwig, and D. S. Pereira. 2004. DEGA/AMIGO-2, a leucine-rich repeat family member, differentially expressed in human gastric adenocarcinoma: Effects on ploidy, chromosomal stability, cell adhesion/migration and tumorigenicity. Oncogene. 23:5056-5067.

Raff, M. C. 1992. Social controls on cell survival and cell death. Nature. 356:397-400.

Raimondi, C., and M. Falasca. 2011. Targeting PDK1 in cancer. Current Medicinal Chemistry. 18:2763-2769.

Ridley, A. J., M. A. Schwartz, K. Burridge, R. A. Firtel, M. H. Ginsberg, G. Borisy, J. T. Parsons, and A. R. Horwitz. 2003. Cell Migration: Integrating Signals from Front to Back. Science. 302:1704-1709.

Sheppard, K. E., K. M. Kinross, B. Solomon, R. B. Pearson, and W. A. Phillips. 2012. Targeting PI3 kinase/AKT/mTOR signaling in cancer. Critical Reviews in Oncogenesis. 17:69-95.

Stroblad, S., and D. A. Cheresh. 1996. Cell adhesion and angiogenesis. Trends in Cell Biology. 6:462-468.

Thompson, C. B. 1995. Apoptosis in the pathogenesis and treatment of disease. Science. 267:1456-1462.

Toker, A., and A. C. Newton. 2000. Cellular signaling: Pivoting around PDK-1. Cell. 103:185-188.

Vicent, D., J. Ilany, T. Kondo, K. Naruse, S. J. Fisher, Y. Y. Kisanuki, S. Bursell, M. Yanagisawa, G. L. King, and C. R. Kahn. 2003. The role of endothelial insulin signaling in the regulation of vascular tone and insulin resistance. Journal of Clinical Investigation. 111:1373-1380.

Vivanco, I., and C. L. Sawyers. 2002. The phosphatidylinositol 3-kinase-AKT pathway in human cancer. Nature Reviews Cancer. 2:489-501.

Wu, Y., Q. Li, and X. Z. Chen. 2007. Detecting protein-protein interactions by Far western blotting. Nature protocols. 2:3278-3284.

Xia, C., Q. Meng, Z. Cao, X. Shi, and B. H. Jiang. 2006. Regulation of angiogenesis and tumor growth by p110 alpha and AKT1 via VEGF expression. Journal of Cellular Physiology. 209:56-66.

Yamada, T., S. Takeuchi, N. Fujita, A. Nakamura, W. Wang, Q. Li, M. Oda, T. Mitsudomi, Y. Yatabe, Y. Sekido, J. Yoshida, M. Higashiyama, M. Noguchi, H. Uehara, Y. Nishioka, S. Sone, and S. Yano. 2013. Akt kinase-interacting protein1, a novel therapeutic target for lung cancer with EGFR-activating and gatekeeper mutations. Oncogene. 32:4427-4435.

Sequences

SEQ ID No: 1

```
mslrvhtlptllgavvrpgcrellcllmitvtvgpgasgvcpta cicatdivsctnknlskvpgnlfrlikrldlsynriglldsewi pvsfaklntlilrhnnitsistgsfsttpnlkcldlssnklktv knavfqelkvlevillynnhisyldpsafgglsqlqklylsgnf ltqfpmdlyvgrfklaelmfldvsynripsmpmhhinlvpgkql rgiylhgnpfvcdcslysllvfwyrrhfssvmdfkndytcrlws dsrhsrqvillqdsfmncsdsiingsfralgfiheaqvgerlmv hcdsktgnantdfiwvgpdnrllepdkemenfyvfhngslvies prfedagvysciamnkqrllnetvdvtinvsnftvsrshaheaf ntafttlaacvasivlvllylyltpcpckcktkrqknmlhqsna hssilspgpasdasaderkagagkrvvfleplkdtaagqngkvr lfpseaviaegilkstrgksdsdsvnsvfsdtpfvast
```

-continued

SEQ ID No: 2

GKRVVFLEPLKDTA

SEQ ID No: 3

YGRKKRRQRRR

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A decoy peptide or polypeptide comprising or consisting of the sequence of amino acid residues 465-474 of SEQ ID NO: 1, wherein the decoy peptide or polypeptide inhibits the binding of adhesion molecule with Ig-like domain 2 (AMIGO2) and 3-phosphoinositide-dependent kinase 1 by competitive inhibition, and the peptide or polypeptide:

(a) consists of residues 465-474 of SEQ ID NO: 1;
(b) consists of residues 465-474 of SEQ ID NO: 1 and (i) up to 20 amino acids in an N-terminal direction or (ii) up to 20 amino acid residues in a C-terminal direction of the sequence of amino acid residues 465-474 of SEQ ID NO: 1;
(c) comprises a protecting group; or
(d) comprises a cell penetrating peptide (CPP).

2. The decoy peptide or polypeptide of claim 1, wherein the decoy peptide or polypeptide consists of residues 465-474 of SEQ ID NO: 1 and up to 20 amino acid residues in an N-terminal direction or up to 20 amino acid residues in a C-terminal direction of the sequence of amino acid residues 465-474 of SEQ ID NO: 1.

3. The decoy peptide or polypeptide of claim 1, wherein the decoy peptide or polypeptide consists of residues 465-474 of SEQ ID NO: 1 and up to 50 amino acid residues in an N-terminal direction or up to 50 amino acid residues in a C-terminal direction of the sequence of amino acid residues 465-474 of SEQ ID NO: 1.

4. The decoy peptide or polypeptide of claim 1, wherein the decoy peptide or polypeptide comprises or consists of SEQ ID NO: 2.

5. The decoy peptide or polypeptide of claim 1, wherein a cell penetrating peptide is bound to the decoy peptide or polypeptide.

6. The decoy peptide or polypeptide of claim 5, wherein the cell penetrating peptide comprises SEQ ID NO: 3.

7. The decoy peptide or polypeptide of claim 1, consisting of (i) residues 465-474 of SEQ ID NO: 1 and one or more optional protecting groups or CPPs, or (ii) SEQ ID NO: 2 and one or more optional protecting groups or CPPs.

8. The decoy peptide or polypeptide of claim 7, consisting of residues 465-474 of SEQ ID NO: 1.

9. The decoy peptide or polypeptide of claim 7, consisting of SEQ ID NO: 2.

10. The decoy peptide or polypeptide of claim 1, consisting of residues 465-474 of SEQ ID NO: 1 and (i) up to 20 amino acids in an N-terminal direction of amino acid residues 465-474 of SEQ ID NO: 1, and optionally one or more protecting groups or CPPs, or (ii) up to 20 amino acid residues in a C-terminal direction of the sequence of amino acid residues 465-474 of SEQ ID NO: 1, and optionally one or more protecting groups or CPPs.

11. The decoy peptide or polypeptide of claim 10, consisting of residues 465-474 of SEQ ID NO: 1 and (i) up to 20 amino acids in an N-terminal direction of amino acid residues 465-474 of SEQ ID NO: 1, and one or more protecting groups or CPPs, or (ii) up to 20 amino acid residues in a C-terminal direction of the sequence of amino acid residues 465-474 of SEQ ID NO: 1, and one or more protecting groups or CPPs.

12. The decoy peptide or polypeptide of claim 10, consisting of residues 465-474 of SEQ ID NO: 1 and (i) up to 20 amino acids in an N-terminal direction of amino acid residues 465-474 of SEQ ID NO: 1, or (ii) up to 20 amino acid residues in a C-terminal direction of the sequence of amino acid residues 465-474 of SEQ ID NO: 1.

13. A pharmaceutical composition for preventing or treating cancer or an angiogenic disease, the pharmaceutical composition comprising: (a) a pharmaceutically effective amount of the decoy peptide or polypeptide of claim 1; and (b) a pharmaceutically acceptable carrier.

14. A method for preventing or treating cancer or an angiogenic disease, the method comprising: (a) a pharmaceutically effective amount of the decoy peptide or polypeptide of claim 1; and (b) a pharmaceutically acceptable carrier.

* * * * *

SEQUENCE LISTING

```
<160> NUMBER OF SEQ ID NOS: 3

<210> SEQ ID NO 1
<211> LENGTH: 522
<212> TYPE: PRT
<213> ORGANISM: Homo sapiens

<400> SEQUENCE: 1

Met Ser Leu Arg Val His Thr Leu Pro Thr Leu Leu Gly Ala Val Val
1               5                   10                  15

Arg Pro Gly Cys Arg Glu Leu Leu Cys Leu Leu Met Ile Thr Val Thr
            20                  25                  30

Val Gly Pro Gly Ala Ser Gly Val Cys Pro Thr Ala Cys Ile Cys Ala
        35                  40                  45

Thr Asp Ile Val Ser Cys Thr Asn Lys Asn Leu Ser Lys Val Pro Gly
    50                  55                  60

Asn Leu Phe Arg Leu Ile Lys Arg Leu Asp Leu Ser Tyr Asn Arg Ile
65                  70                  75                  80

Gly Leu Leu Asp Ser Glu Trp Ile Pro Val Ser Phe Ala Lys Leu Asn
                85                  90                  95

Thr Leu Ile Leu Arg His Asn Asn Ile Thr Ser Ile Ser Thr Gly Ser
            100                 105                 110

Phe Ser Thr Thr Pro Asn Leu Lys Cys Leu Asp Leu Ser Ser Asn Lys
        115                 120                 125

Leu Lys Thr Val Lys Asn Ala Val Phe Gln Glu Leu Lys Val Leu Glu
    130                 135                 140

Val Leu Leu Leu Tyr Asn Asn His Ile Ser Tyr Leu Asp Pro Ser Ala
145                 150                 155                 160

Phe Gly Gly Leu Ser Gln Leu Gln Lys Leu Tyr Leu Ser Gly Asn Phe
                165                 170                 175

Leu Thr Gln Phe Pro Met Asp Leu Tyr Val Gly Arg Phe Lys Leu Ala
            180                 185                 190

Glu Leu Met Phe Leu Asp Val Ser Tyr Asn Arg Ile Pro Ser Met Pro
        195                 200                 205

Met His His Ile Asn Leu Val Pro Gly Lys Gln Leu Arg Gly Ile Tyr
    210                 215                 220

Leu His Gly Asn Pro Phe Val Cys Asp Cys Ser Leu Tyr Ser Leu Leu
225                 230                 235                 240

Val Phe Trp Tyr Arg Arg His Phe Ser Ser Val Met Asp Phe Lys Asn
                245                 250                 255

Asp Tyr Thr Cys Arg Leu Trp Ser Asp Ser Arg His Ser Arg Gln Val
            260                 265                 270

Leu Leu Leu Gln Asp Ser Phe Met Asn Cys Ser Asp Ser Ile Ile Asn
        275                 280                 285

Gly Ser Phe Arg Ala Leu Gly Phe Ile His Glu Ala Gln Val Gly Glu
    290                 295                 300

Arg Leu Met Val His Cys Asp Ser Lys Thr Gly Asn Ala Asn Thr Asp
305                 310                 315                 320
```

```
Phe Ile Trp Val Gly Pro Asp Asn Arg Leu Leu Glu Pro Asp Lys Glu
                325                 330                 335

Met Glu Asn Phe Tyr Val Phe His Asn Gly Ser Leu Val Ile Glu Ser
            340                 345                 350

Pro Arg Phe Glu Asp Ala Gly Val Tyr Ser Cys Ile Ala Met Asn Lys
        355                 360                 365

Gln Arg Leu Leu Asn Glu Thr Val Asp Val Thr Ile Asn Val Ser Asn
    370                 375                 380

Phe Thr Val Ser Arg Ser His Ala His Glu Ala Phe Asn Thr Ala Phe
385                 390                 395                 400

Thr Thr Leu Ala Ala Cys Val Ala Ser Ile Val Leu Val Leu Leu Tyr
                405                 410                 415

Leu Tyr Leu Thr Pro Cys Pro Cys Lys Cys Lys Thr Lys Arg Gln Lys
            420                 425                 430

Asn Met Leu His Gln Ser Asn Ala His Ser Ser Ile Leu Ser Pro Gly
            435                 440                 445

Pro Ala Ser Asp Ala Ser Ala Asp Glu Arg Lys Ala Gly Ala Gly Lys
        450                 455                 460

Arg Val Val Phe Leu Glu Pro Leu Lys Asp Thr Ala Ala Gly Gln Asn
465                 470                 475                 480

Gly Lys Val Arg Leu Phe Pro Ser Glu Ala Val Ile Ala Glu Gly Ile
                485                 490                 495

Leu Lys Ser Thr Arg Gly Lys Ser Asp Ser Asp Ser Val Asn Ser Val
            500                 505                 510

Phe Ser Asp Thr Pro Phe Val Ala Ser Thr
            515                 520

<210> SEQ ID NO 2
<211> LENGTH: 14
<212> TYPE: PRT
<213> ORGANISM: Artificial Sequence
<220> FEATURE:
<223> OTHER INFORMATION: Synthetic construct

<400> SEQUENCE: 2

Gly Lys Arg Val Val Phe Leu Glu Pro Leu Lys Asp Thr Ala
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic construct

<400> SEQUENCE: 3

Tyr Gly Arg Lys Lys Arg Arg Gln Arg Arg
1               5                   10
```